United States Patent
Tanabe et al.

(10) Patent No.: US 12,195,764 B2
(45) Date of Patent: Jan. 14, 2025

(54) METHOD FOR CULTURING CELLS INTO WHICH REPROGRAMMING FACTOR IS INTRODUCED

(71) Applicants: I Peace, Inc., Palo Alto, CA (US); Koji Tanabe, Palo Alto, CA (US)

(72) Inventors: Koji Tanabe, Palo Alto, CA (US); Kenta Suto, Palo Alto, CA (US)

(73) Assignee: I Peace, Inc., Palo Alto, CA (US)

( * ) Notice: Subject to any disclaimer, the term of this patent is extended or adjusted under 35 U.S.C. 154(b) by 0 days.

(21) Appl. No.: 17/646,398

(22) Filed: Dec. 29, 2021

(65) Prior Publication Data

US 2022/0213446 A1 Jul. 7, 2022

Related U.S. Application Data

(60) Provisional application No. 63/131,451, filed on Dec. 29, 2020.

(51) Int. Cl.
C12N 5/074 (2010.01)
C12N 5/00 (2006.01)

(52) U.S. Cl.
CPC ......... C12N 5/0696 (2013.01); C12N 5/0025 (2013.01)

(58) Field of Classification Search
CPC ............................. C12N 5/0696; C12N 5/0025
See application file for complete search history.

(56) References Cited

U.S. PATENT DOCUMENTS

| | | | |
|---|---|---|---|
| 9,404,124 B2 | 8/2016 | Okita et al. | |
| 2007/0020754 A1* | 1/2007 | Yuge | A61P 35/02 435/325 |
| 2011/0143397 A1 | 6/2011 | Kariko et al. | |
| 2011/0287538 A1 | 11/2011 | Fusaki et al. | |
| 2012/0196360 A1 | 8/2012 | Okita et al. | |
| 2013/0195812 A1 | 8/2013 | Kikyo et al. | |
| 2013/0210150 A1 | 8/2013 | Ban et al. | |
| 2013/0302295 A1 | 11/2013 | Wang et al. | |
| 2014/0242695 A1 | 8/2014 | Wang et al. | |
| 2014/0328825 A1 | 11/2014 | Meis et al. | |
| 2015/0232810 A1 | 8/2015 | Luo et al. | |
| 2016/0215270 A1 | 7/2016 | Ban et al. | |
| 2016/0263233 A1 | 9/2016 | Wang et al. | |
| 2019/0328835 A1 | 10/2019 | Zischka et al. | |
| 2020/0385687 A1 | 12/2020 | Tanabe et al. | |

FOREIGN PATENT DOCUMENTS

| | | | |
|---|---|---|---|
| EP | 1 186 667 A1 | 3/2002 | |
| JP | 2013-501505 A | 1/2013 | |
| JP | 2013-512690 A | 4/2013 | |
| JP | 5376478 B2 | 12/2013 | |
| JP | 2015-517311 A | 6/2015 | |
| JP | 2015-522257 A | 8/2015 | |
| JP | 2017-503849 A | 2/2017 | |
| JP | 2018-538306 A | 12/2018 | |
| WO | 2000/070070 A1 | 11/2000 | |
| WO | 2010/008054 A1 | 1/2010 | |
| WO | 2012/029770 A1 | 3/2012 | |
| WO | 2015/046229 A1 | 4/2015 | |
| WO | 2018/155595 A1 | 8/2018 | |

OTHER PUBLICATIONS

Willmann et al. To Clone or Not to Clone? Induced Pluripotent Stem Cells Can Be Generated in Bulk Culture. PLoS One. 2013; 8(5): e65324, p. 1-9. (Year: 2013).*
Mosqueira et al. CRISPR/Cas9 editing in human pluripotent stem cell-cardiomyocytes highlights arrhythmias, hypocontractility, and energy depletion as potential therapeutic targets for hypertrophic cardiomyopathy. European Heart Journal. 2018; 39: 3879-3892 and suppl p. 1-20. (Year: 2018).*
Zhou et al. Generation of Induced Pluripotent Stem Cells from Urine. J Am Soc Nephrol. 2011; 22: 1221-1228. (Year: 2011).*
Miura et al. Generation of Mouse and Human Organoid-Forming Intestinal Progenitor Cells by Direct Lineage Reprogramming. Cell Stem Cell. 2017; 21: 456-471. (Year: 2017).*
Dorrenhaus et al., Arch Toxicol. 2000; 74: 618-626. (Year: 2000).*
Gaignerie et al. Urine-derived cells provide a readily accessible cell type for feeder-free mRNA reprogramming. Scientific Reports. 2018; 8: 14363, p. 1-10. (Year: 2018).*
Hiroyuki Hirai et al. "Radical Acceleration of Nuclear Reprogramming by Chromatin Remodeling with the Transactivation Domain of MyoD" Stem Cells, 2011, pp. 1349-1361, vol. 29.
Hiroyuki Hirai et al. "Efficient iPS Cell Production with the MyoD Transactivation Domain in Serum-Free Culture" PLoS One, Mar. 2012, pp. 1-9, vol. 7 No. 3, e34149.
Keisuke Okita et al. "Generation of Germline-Competent Induced Pluripotent Stem Cells" nature, Jul. 19, 2007, pp. 313-317, vol. 448.
Kenji Osafune et al. "Marked Differences in Differentiation Propensity Among Human Embryonic Stem Cell Lines" nature biotechnology, Mar. 2008, 448, pp. 313-315, vol. 26 No. 3.
Praopilas Phakdeeindan et al. "Rabbit Induced Pluripotent Stem Cells Retain Capability of in vitro Cardiac Differentiation" Experimental Animals, 2019, pp. 35-47, vol. 68 No. 1, DOI: 10.1538/expanim.18-0074.

(Continued)

Primary Examiner — Taeyoon Kim
Assistant Examiner — Jianjian Zhu
(74) Attorney, Agent, or Firm — Studebaker & Brackett PC

(57) ABSTRACT

According to the present disclosure, there is provided a method for culturing cells into which a reprogramming factor is introduced including culturing cells into which a reprogramming factor is introduced; and recovering all cells into which the reprogramming factor is introduced and seeding and passaging at least part of the recovered cells in a medium. In addition, there is provided a method for culturing cells into which a reprogramming factor is introduced, including culturing cells into which a reprogramming factor is introduced; and inducing somatic cells different from pluripotent stem cells without passaging the cells into which the reprogramming factor is introduced.

18 Claims, 42 Drawing Sheets

(56) References Cited

OTHER PUBLICATIONS

Narae Kim et al. "Immobilized pH in Culture Reveals an Optimal Condition for Somatic Cell Reprogramming and Differentiation of Pluripotent Stem Cells" Reproductive Medicine and Biology, 2017, pp. 58-66, vol. 16, DOI: 10-1002/rmb2.12011.

Ling-Bo Wang et al. "The Effect of Mouse Cell Seeding Density on the Efficiency of iPS Cell Derivation" Acta Agriculturae Universitatis Jiangxiensis, 2010, pp. 868-875, vol. 32 No. 5.

* cited by examiner

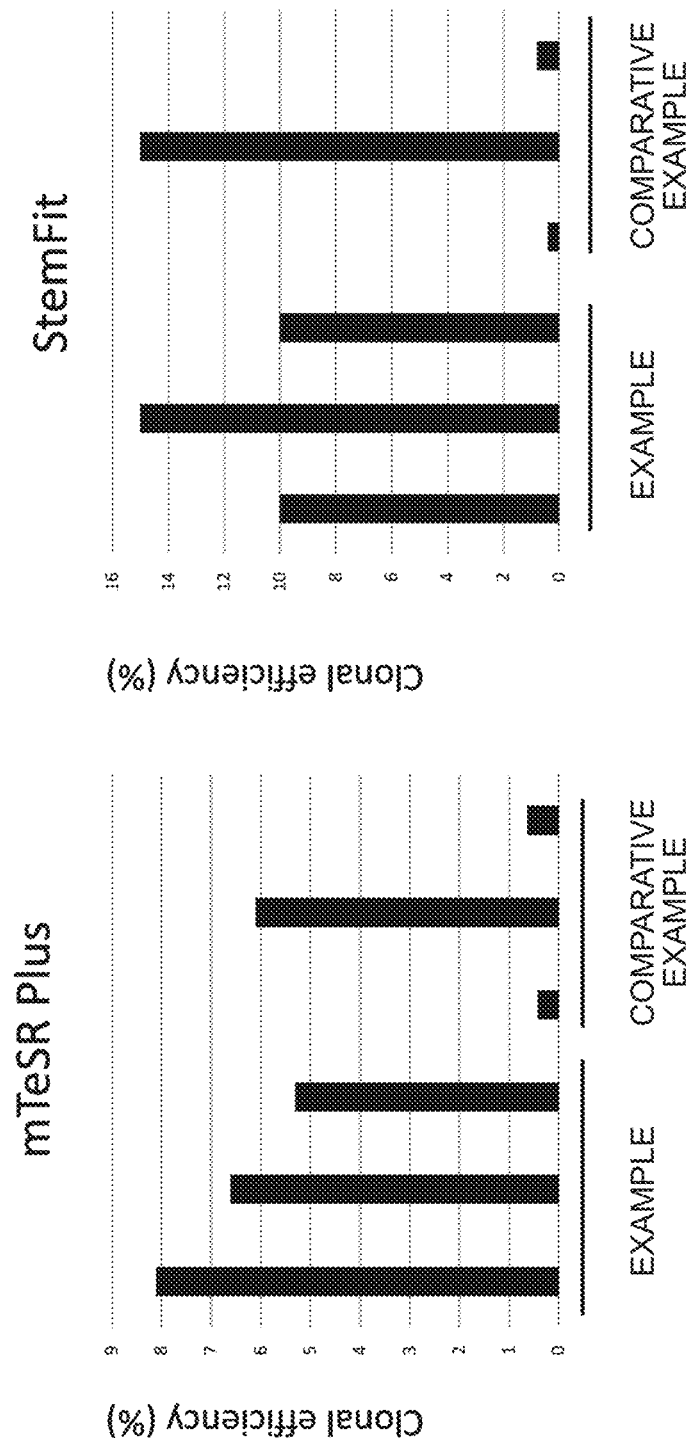

FIG. 8

| | OCCURRENCE OF MYOCARDIAL PULSATION | | |
|---|---|---|---|
| | TEST1 | TEST2 | TEST3 |
| WOC1 | YES | YES | |
| WOC2 | YES | YES | |
| WOC3 | YES | YES | |
| C1 | NO | NO | NO |
| C2 | NO | NO | YES |
| C3 | YES | YES | YES |

WOC1-WOC3: EXAMPLE
C1-C3: COMPARATIVE EXAMPLE

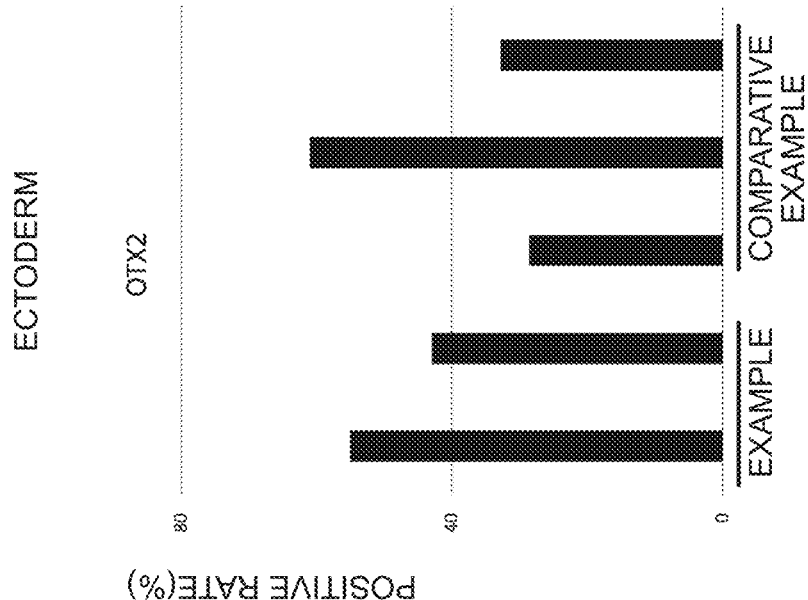
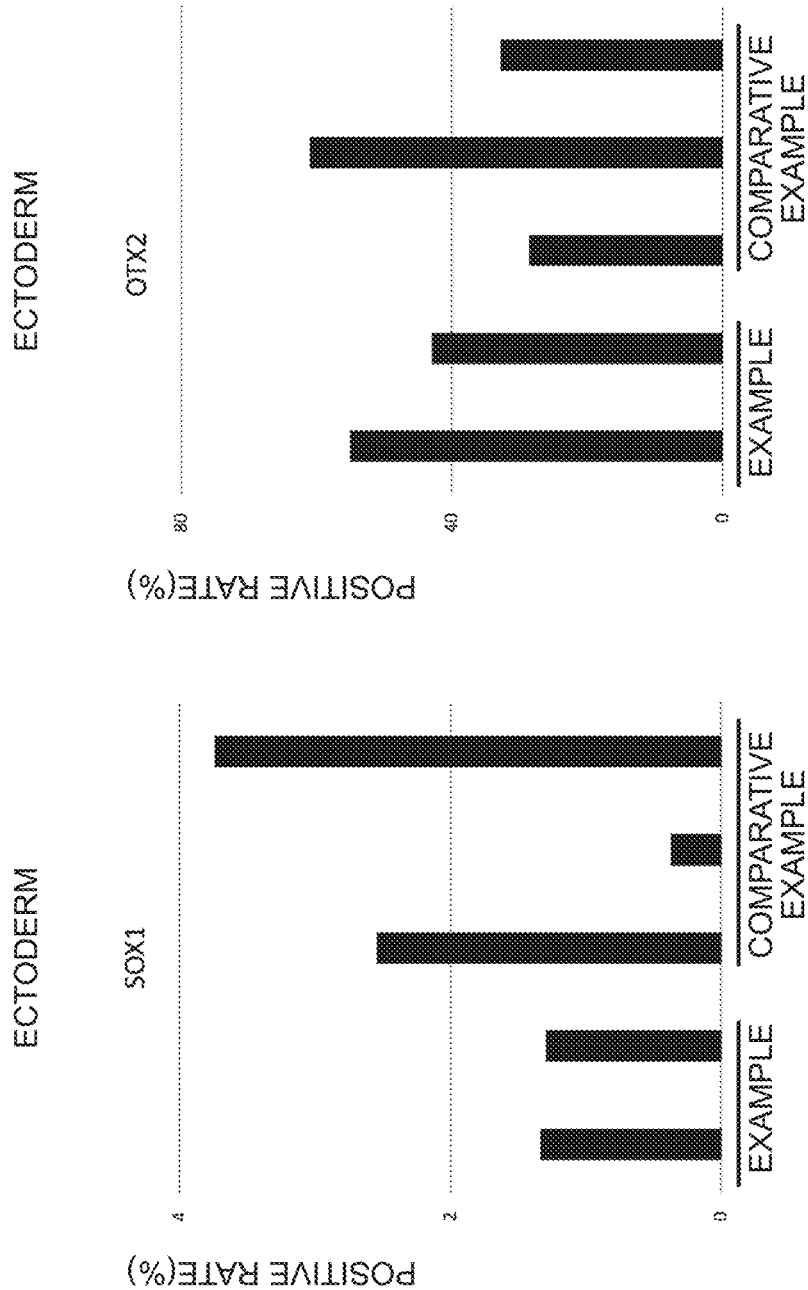

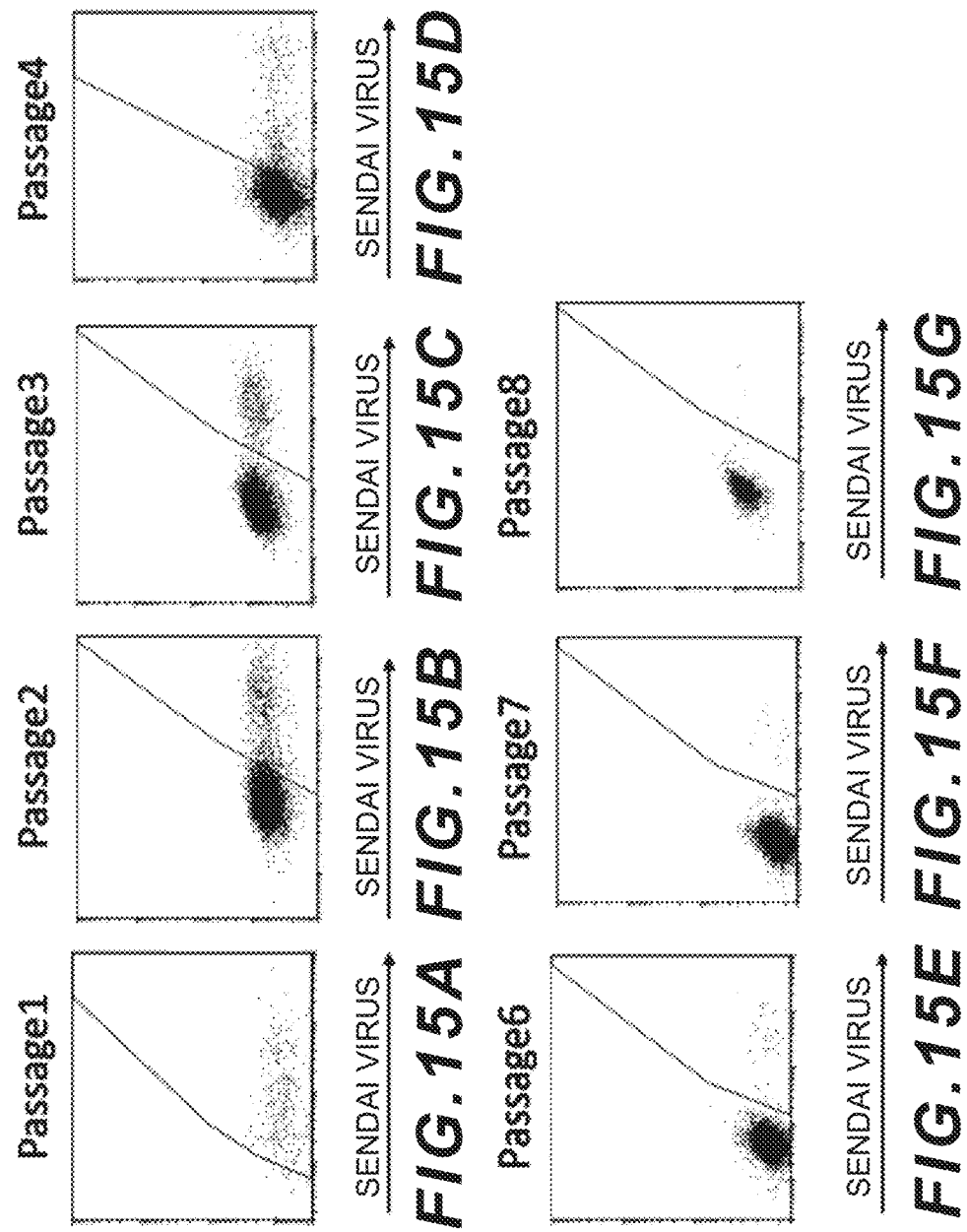

TRA-1-60

SENDAI VIRUS

Lane 1:REFERENCE EXAMPLE 1
Lane 2:REFERENCE EXAMPLE 6
Lane 3:Positive control
Lane 4:Negative control

SECRETORY TISSUE-LIKE STRUCTURE

NEURAL TUBE-LIKE STRUCTURE

INTESTINAL TRACT-LIKE STRUCTURE

CARTILAGE AND BONE-LIKE STRUCTURE

TRA 1-60

TRA-1-60

METHOD FOR CULTURING CELLS INTO WHICH REPROGRAMMING FACTOR IS INTRODUCED

BACKGROUND

Field

The present invention relates to a cell technology, and a method for culturing cells into which a reprogramming factor is introduced.

Description of Related Art

Induced pluripotent stem (iPS) cells are cells having two characteristic abilities. One is an ability to transform into all the cells that constitute a body. The other is to have a semi-permanent proliferative ability. Since iPS cells have these two abilities, they can be applied to a transplantation treatment without rejection by producing iPS cells from their own somatic cells and converting them into target somatic cells. Therefore, iPS cells are considered to be a promising technology for regenerative medicine (for example, refer to WO 2000/70070, WO 2010/008054, WO 2012/029770, WO 2015/046229, Nature 448, 313-317 and Nature Biotechnol 26(3):313-315, 2008). In the related art, when a reprogramming factor is introduced into cells to induce iPS cells, stem cell-like colonies are picked up with a pipette and passaged while being observed under a microscope or the like.

SUMMARY

There is demand for a method for efficiently culturing cells into which a reprogramming factor is introduced. One object of the present invention is to provide a method for efficiently culturing cells into which a reprogramming factor is introduced.

According to an aspect of the present invention, there is provided a method for culturing cells into which a reprogramming factor is introduced, including culturing cells into which the reprogramming factor is introduced, and recovering all cells into which the reprogramming factor is introduced and seeding and passaging at least part of the recovered cells in a medium. All of the recovered cells may be mixed.

In the method, cells may not be cloned in the passage.

The method may not include isolating a plurality of colonies formed by the cells into which the reprogramming factor is introduced from each other.

The method may not include cloning a single colony formed by the cells into which the reprogramming factor is introduced.

The method may not include picking up colonies formed by the cells into which the reprogramming factor is introduced.

In the method, all cells attached to a culture vessel, which are the cells into which the reprogramming factor is introduced, may be recovered, and at least part of the recovered cells may be seeded in a medium.

In the method, the cells into which the reprogramming factor is introduced may be passaged without distinguishing them according to a gene expression state.

In the method, the cells into which the reprogramming factor is introduced may be passaged without distinguishing them according to the degree of reprogramming.

The method may further include culturing and expanding the cells into which a reprogramming factor is introduced in two-dimensional culture.

The method may further include culturing and expanding the cells into which a reprogramming factor is introduced in three-dimensional culture.

The method may further include generating stem cells from the cells into which a reprogramming factor is introduced.

The method may further include freezing the cells into which the reprogramming factor is introduced.

The method may further include differentiating the cells into which the reprogramming factor is introduced into at least one selected from among the endoderm, the mesoderm, and the ectoderm.

The method may further include forming at least one selected from among embryoid bodies, organoids, and spheres from the cells into which the reprogramming factor is introduced.

The method may further include inducing somatic cells different from pluripotent stem cells from the cells into which the reprogramming factor is introduced.

The method may further include, after a process for inducing the somatic cells, cloning the processed cells.

The method may further include performing a gene editing treatment on the cells into which the reprogramming factor is introduced.

In the method, the cells into which the reprogramming factor is introduced may be derived from blood cells or fibroblasts.

In the method, the cells into which the reprogramming factor is introduced may be cells contained in urine.

In the method, the cells into which the reprogramming factor is introduced may be bladder epithelial cells.

The method may further include collecting the cells into which the reprogramming factor is to be introduced from urine.

In the method, the cells into which the reprogramming factor is introduced may be derived from a plurality of humans or a plurality of non-human animals.

In the method, the cells into which the reprogramming factor is introduced may be cultured in a closed culture vessel.

In the method, during passage, seeding may be performed at a low concentration.

In the method, the low concentration may be 0 $0.25\times10^4$ cells/cm$^2$ or less.

In the method, the low concentration may be a concentration at which 11 or more seeded cells do not come into contact with each other.

In the method, the low concentration may be 5% or less confluence.

In the method, the reprogramming factor may be RNA.

In the method, the reprogramming factor may be introduced into cells by a lipofection method.

In the method, the reprogramming factor may be introduced into cells using a viral vector.

In the method, the viral vector may be an RNA viral vector.

In the method, the RNA viral vector may be a Sendai virus vector.

In addition, according to an aspect of the present invention, there is provided a method for culturing cells into which a reprogramming factor is introduced, including culturing cells into which a reprogramming factor is introduced; and inducing somatic cells different from pluripotent stem cells from the cells into which the reprogramming factor is introduced without passing.

The method may further include culturing and expanding the cells into which a reprogramming factor is introduced in two-dimensional culture.

The method may further include culturing and expanding the cells into which a reprogramming factor is introduced in three-dimensional culture.

The method may further include freezing the cells into which the reprogramming factor is introduced.

The method may further include differentiating the cells into which the reprogramming factor is introduced into at least one selected from among the endoderm, the mesoderm, and the ectoderm.

The method may further include performing a gene editing treatment on the cells into which the reprogramming factor is introduced.

In the method, the cells into which the reprogramming factor is introduced may be derived from blood cells or fibroblasts.

In the method, the cells into which the reprogramming factor is introduced may be derived from a plurality of humans or a plurality of non-human animals.

In the method, the cells into which the reprogramming factor is introduced may be cultured in a closed culture vessel.

In the method, the reprogramming factor may be RNA.

In the method, the reprogramming factor may be introduced into cells by a lipofection method.

In the method, the reprogramming factor may be introduced into cells using a viral vector.

In the method, the viral vector may be an RNA viral vector.

In the method, the RNA viral vector may be a Sendai virus vector.

According to the present invention, it is possible to provide a method for efficiently culturing cells into which a reprogramming factor is introduced.

BRIEF DESCRIPTION OF DRAWINGS

FIGS. 4A and 4B shows graphs of clonal efficiency according to Example 1 and Comparative Example 1;

FIG. 8 is a table showing presence or absence of myocardial pulsation according to Example 4 and Comparative Example 4;

FIGS. 11A and 11B shows graphs of the positive rate of SOX1 and the positive rate of OTX2 according to Example 6 and Comparative Example 6;

FIGS. 15A to 15G shows graphs of the measurement results obtained by a flow cytometer according to Reference Example 2;

FIGS. 38A to 38D shows images of urine-derived cells into which reprogramming factors were introduced according to Example 13;

DETAILED DESCRIPTION

Figure 1A:
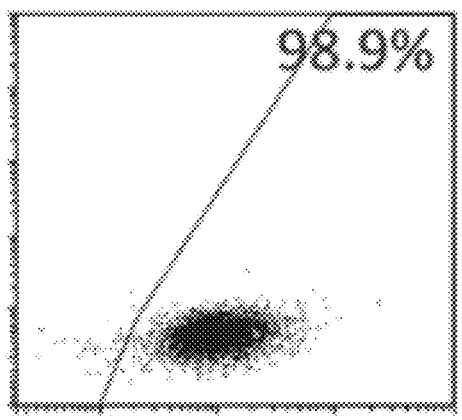
FIGS. 1A and 1B shows graphs of the measurement results obtained by a flow cytometer according to Example 1.

Embodiments of the present invention will be described below in detail. Here, the following embodiments exemplify a device and a method for embodying the technical ideas of the invention, and the technical ideas of the invention do not specify the combination of constituent members or the like as in the following. The technical ideas of the invention can be variously modified within the scope of the claims.

A method for culturing cells into which a reprogramming factor is introduced according to an embodiment includes culturing cells into which a reprogramming factor is introduced, and recovering all cells into which the reprogramming factor is introduced and seeding and passaging at least part of the recovered cells in a medium. For example, pluripotent stem cells are induced from cells into which the reprogramming factor is introduced. The pluripotent stem cells are, for example, iPS cells.

The cells into which the reprogramming factor is introduced are not particularly limited, and examples thereof include fibroblasts, blood cells, dental pulp stem cells, keratinocytes, dermal papilla cells, oral epithelial cells, and somatic prestem cells. The cells into which the reprogramming factor is introduced may be cells contained in urine. Examples of the cells contained in urine include bladder epithelial cells. The cells into which the reprogramming factor is introduced may be cells derived from humans or derived from non-human animals. The cells into which the reprogramming factor is introduced may be derived from one human or derived from a plurality of humans. The cells into which the reprogramming factor is introduced may be derived from one non-human animals or derived from a plurality of non-human animals.

The blood cells are isolated from blood. The blood is, for example, peripheral blood and cord blood, but is not limited thereto. The blood may be collected from an adult or a minor. During blood sampling, an anticoagulant such as ethylene-diamine-tetraacetic acid (EDTA), heparin, and a biological preparation standard blood preservative solution A (ACD-A) is used.

The blood cells are nucleated cells, for example, mononuclear cells (monocytes), neutrophils, macrophages, eosinophils, basophils, and lymphocytes, and do not include red blood cells, granulocytes, and platelets. The blood cells may be, for example, endothelial progenitor cells, blood stem/progenitor cells, T cells, or B cells. T cells are, for example, αβT cells.

The mononuclear cells are isolated from blood using a medium for isolating blood cells, a centrifugal device or the like. A method for isolating mononuclear cells in the case where Ficoll (GE Healthcare) is used as a medium for isolating blood cells is as follows.

Since the isolation accuracy of mononuclear cells tends to deteriorate at a low temperature, the centrifuge is set at 4° C. to 42° C., preferably 18° C. 10 μL to 50 mL of blood is sampled from an adult or minor human, a chelating agent containing EDTA being added to the blood to prevent the blood from coagulating, and is mixed gently. In addition, 5 mL of a medium for isolating human lymphocytes (Ficoll-Paque PREMIUM, GE Healthcare Japan) is dispensed into two 15 mL tubes. 5 mL of PBS is added to 5 mL of the blood for dilution, and 5 mL layers are placed on the medium for isolating human lymphocytes in each of the tubes. In this case, the diluted blood is slowly added onto the medium along the tube wall of the tube to prevent disturbance of the interface.

The solution in the tube is centrifuged at 10×g to 1,000×g, and preferably, 400×g, at 4° C. to 42° C., preferably 18° C., for 5 minutes to 2 hours, preferably for 30 minutes. After centrifugation, a cloudy white intermediate layer appears in the tube. The cloudy white intermediate layer contains mononuclear cells. The cloudy white intermediate layer in the tube is slowly recovered with a Pipeteman and is transferred to a new 15 mL tube. In this case, the lower layer should not be sucked up. About 1 mL of the cloudy white intermediate layer can be recovered from one tube. Two intermediate layers are transferred together into one tube.

1 mL to 48 mL, preferably 12 mL of PBS is added to the recovered mononuclear cells, and the solution is additionally centrifuged at 10×g to 1,000×g, preferably 200×g, at 4° C. to 42° C., preferably 18° C., for 1 minute to 60 minutes, preferably 10 minutes. Then, the supernatant of the solution is sucked up and removed using an aspirator, and 1 mL to 12 mL, preferably 3 mL of a serum-free hematopoietic cell medium of known composition (X-VIVO (registered trademark) 10, Lonza) is added for suspension therein to obtain a mononuclear cell suspension. Of this, 10 μL of a mononuclear cell suspension is stained with trypan blue and counting is performed on a hemacytometer.

A method for isolating mononuclear cells in the case where a Vacutainer (registered trademark, BD) is used as a blood collection tube is as follows.

Since the isolation accuracy of mononuclear cells tends to deteriorate at a low temperature, the centrifuge is set to 4° C. to 42° C., preferably 18° C. 8 mL of blood is sampled from an adult or minor human using a blood collection tube (Vacutainer (registered trademark), BD), mixed by inversion and mixed with an anticoagulant. Then, the balance is adjusted, and the solution is centrifuged at 4° C. to 42° C., preferably 18° C., at 100×g to 3,000×g, preferably 1,500×g to 1,800×g with a swing rotor for 1 minute to 60 minutes, preferably 20 minutes. After centrifugation, the upper layer, which is a plasma layer, is removed and pipetting is performed to suspend the mononuclear cell layer and blood cells adhered to the gel to obtain a suspension. The obtained suspension is transferred to another 15 mL tube.

1 mL to 14 mL, preferably 12 mL of PBS is added to the suspension in a 15 mL tube, and the suspension is centrifuged at 4° C. to 42° C., preferably 18° C., at 100×g to 3,000×g, preferably 200×g for 1 minute to 60 minutes, preferably 5 minutes. After centrifugation, the supernatant is removed with an aspirator. In addition, a hemolytic agent (PharmLyse (registered trademark), 10-fold concentration, BD) is diluted to a 1-fold concentration with sterilized water. The pellet in the 15 mL tube is loosened by tapping, and 1 mL to 14 mL, preferably 1 mL of a hemolytic agent is added. Then, light is blocked therefrom and the solution is left for 1 minute to 60 minutes, preferably 1 minute at room temperature.

Next, 1 mL to 14 mL, preferably 12 mL of PBS is added to a 15 mL tube, and centrifugation is performed at 4° C. to 42° C., preferably room temperature, at 100×g to 3,000×g, preferably 200×g for 1 minute to 60 minutes, preferably 5 minutes. After centrifugation, the supernatant is removed with an aspirator, 1 mL to 15 mL, and preferably 3 mL of a serum-free hematopoietic cell medium of known composition (X-VIVO (registered trademark) 10, Lonza) is added for suspension therein to obtain a mononuclear cell suspension. Of this, 10 μL of a mononuclear cell suspension is stained with trypan blue and counting is performed on a hemacytometer.

The methods for isolating the mononuclear cells from the blood are not limited to the above methods, and for example, mononuclear cells may be isolated from blood using a dialysis membrane. In addition, a pure cell select system for whole blood mononuclear cell concentration (registered trademark, PALL), a purifier for removing blood cell cells (Cellsorba E, registered trademark, Asahi Kasei), and a filter such as a white blood cell removal filter for platelet preparation (Sepacell PL, registered trademark, PLX-5B-SCD, Asahi Kasei) can also be used.

The mononuclear cells may be isolated using a red blood cell isolating agent that can isolate nucleated cells by gravitational precipitation or centrifugation of red blood cells. Examples of red blood cell isolating agents include HetaSep (registered trademark, STEMCELL Technologies) and HES40 (NIPRO).

In addition, CTL-UP1 (commercially available from Cellular Technology Limited), PBMC-001 (commercially available from Sanguine Biosciences), or the like may be used as the mononuclear cells.

Alternatively, regarding the blood cells, blood cells that are cryopreserved using a cell cryopreservation solution such as Cellbanker 1, Stem-Cellbanker GMP grade, or Stem-Cellbanker DMSO free GMP grade (ZENOAQ) may be thawed and used.

When thawing the mononuclear cells, first, 1 mL to 15 mL, preferably 8 mL of a serum-free hematopoietic cell medium of known composition (X-VIVO (registered trademark) 10, Lonza) is put into a 15 mL tube, the tube containing the frozen mononuclear cells is placed in a warm bath at 4° C. to 42° C., preferably 37° C., and the mononuclear cells start to be thawed. Then, with the remaining ice, the tube containing the mononuclear cells is pulled out of the warm bath, and the mononuclear cells are transferred to a tube containing a serum-free hematopoietic cell medium of known composition. Of this, 10 μL of a mononuclear cell suspension is stained with trypan blue and counting is performed on a hemacytometer.

The blood cells may be isolated based on a cell surface marker. Blood stem/progenitor cells are positive for CD34. T cells are positive for any of CD3, CD4, and CD8. B cells are positive for any of CD10, CD19, and CD20. Macrophages are positive for any of CD11b, CD68, and CD163. Blood stem/progenitor cells, T cells, or B cells are isolated from blood cells using, for example, an automatic magnetic cell isolating device and immunomagnetic beads. Alternatively, mononuclear cells isolated in advance may be prepared. However, blood cells that are not isolated based on a cell surface marker may be used.

CD34 positive cells are stem/progenitor cells, and tend to be easily reprogrammed. In addition, when iPS cells are prepared using T cells which are CD3 positive cells, since the iPS cells derived from T cells maintain a TCR combination type, differentiation into T cells tends to be efficiently induced.

A method for isolating CD34 positive cells is as follows.

10 μL of IL-6 (100 μg/mL), 10 μL of SCF (300 μg/mL), 10 μL of TPO (300 μg/mL), 10 μL of FLT3 ligands (300 μg/mL), and 10 μL of IL-3 (10 μg/mL) are added to 10 mL of a serum-free medium (StemSpan H3000, STEMCELL Technologies) to prepare a blood cell medium (blood stem/progenitor cell medium).

1 mL to 6 mL, preferably 2 mL of a blood cell medium is put into one well of a 6-well plate. In addition, in order to prevent evaporation of the medium, 1 mL to 6 mL, preferably 2 mL of PBS are put into the other five wells. Then, the 6-well plate is placed in an incubator at 4° C. to 42° C., preferably 37° C. for warming.

10 μL to 1 mL, preferably 80 μL of EDTA (500 mmol/L) and 10 μL to 1 mL, preferably 200 μL of FBS are added to 20 mL of PBS to prepare a column buffer. A mononuclear cell suspension containing $1 \times 10^4$ to $1 \times 10^9$, preferably $2 \times 10^7$ mononuclear cells is dispensed in a 15 mL tube, and the mononuclear cell suspension is centrifuged at 4° C. to 42° C., preferably 4° C., at 100×g to 3,000×g, preferably 300×g for 10 minutes. After centrifugation, the supernatant is removed, and the mononuclear cells are suspended in 100 μL to 1 mL, preferably 300 μL of the column buffer.

10 μL to 1 mL, preferably 100 μL of an FcR blocking reagent (Miltenyi Biotec) and 10 μL to 1 mL, preferably 100 μL of a CD34 microbeads kit (Miltenyi Biotec) are added to the mononuclear cell suspension in the 15 mL tube. The FcR blocking reagent is used to increase the specificity of the microbead labeling. Then, the mononuclear cell suspension is mixed and left at 4° C. to 42° C., preferably 4° C. for 1 minute to 2 hours, preferably 30 minutes.

Next, 1 mL to 15 mL, preferably 10 mL of the column buffer is added to the mononuclear cell suspension in the 15 mL tube and diluted, and centrifugation is performed at 4° C. to 42° C., preferably 4° C., at 100×g to 1,000×g, preferably 300×g for 1 minute to 2 hours, preferably 10 minutes. After centrifugation, the supernatant in the 15 mL tube is removed with an aspirator, and 10 μL to 10 mL, preferably 500 μL of the column buffer is added for resuspension therein.

A column for an automatic magnetic cell isolating device (MS column, Miltenyi Biotec) is attached to an automatic magnetic cell isolating device (MiniMACS Separation Unit, Miltenyi Biotec), and 10 μL to 10 mL, preferably 500 μL of the column buffer is put into the column for washing. Next, the mononuclear cells are put into the column. In addition, 10 μL to 10 mL, preferably 500 μL of the column buffer is put into the column, and the column is washed 1 to 10 times, preferably 3 times. Then, the column is removed from the automatic magnetic cell isolating device and put into a 15 mL tube. Next, 10 μL to 10 mL, preferably 1,000 μL of the column buffer is put into the column, and the syringe is immediately pushed to discharge CD34 positive cells to the 15 mL tube.

10 μL of a CD34 positive cell suspension is stained with trypan blue and the number of cells is counted on a blood cell counting chamber. In addition, the CD34 positive cell suspension in the 15 mL tube is centrifuged at 4° C. to 42° C., preferably 4° C., at 100×g to 1,000×g, preferably 300×g for 1 minute to 2 hours, preferably 10 minutes. After centrifugation, the supernatant is removed with an aspirator. In addition, CD34 positive cells are re-suspended in the warmed blood cell medium and the CD34 positive cells are sprinkled on a culture plate. Then, the CD34 positive cells are cultured for 6 days at 4° C. to 42° C., preferably 37° C., 1% to 20%, preferably 5% $CO_2$. During this time, the medium does not have to be replaced.

A method for isolating cells with a marker other than CD34 is similar to the method for isolating the CD34 positive cells.

The reprogramming factor introduced into cells is, for example, RNA. RNA is, for example, mRNA. Examples of reprogramming factors introduced into cells include OCT mRNA such as OCT3/4, SOX mRNA such as SOX2, KLF mRNA such as KLF4, and MYC mRNA such as c-MYC. As the reprogramming factor RNA, $M_3O$ which is improved OCT3/4 may be used. In addition, the reprogramming factor RNA may further include mRNA of at least one factor selected from the group consisting of LIN28A, FOXH1, LIN28B, GLIS1, p53-dominant negative, p53-P275S, L-MYC, NANOG, DPPA2, DPPA4, DPPA5, ZIC3, BCL-2, E-RAS, TPT1, SALL2, NAC1, DAX1, TERT, ZNF206, FOXD3, REX1, UTF1, KLF2, KLF5, ESRRB, miR-291-3p, miR-294, miR-295, NR5A1, NR5A2, TBX3, MBD3sh, TH2A, TH2B, and P53DD. These mRNAs are available from TriLink. It should be noted that, although the gene symbols are described here as those of humans, it is not intended to limit the species by uppercase or lowercase letters. For example, description in all uppercase letters does not exclude inclusion of mouse or rat genes. However, in the examples, the gene symbols are shown according to the species actually used.

p53 is a tumor suppressor protein. The dominant negative mutant of p53 is not particularly limited as long as it can act competitively with a wild type p53 protein in somatic cells and inhibit a function of the wild type p53 protein. Examples of dominant negative mutants of p53 include p53P275S in which proline at position 275 (at position 278 in the case of humans) located in a DNA binding region of mouse p53 is point-mutated to serine, p53DD in which an amino acid at position 14-301 of mouse p53 (corresponding to position 11-304 in human p53) is deficient, p53S58A in which serine at position 58 of mouse p53 (at position 61 in the case of humans) is point-mutated to alanine, p53C135Y in which cysteine at position 135 of human p53 (at position 132 in the case of mice) is point-mutated to tyrosine, p53A135V in which alanine at position 135 of mouse p53 (at position 138 in the case of humans) is point-mutated to valine, p53R172H in which arginine at position 172 of mouse p53 (at position 175 in the case of humans) is point-mutated to histidine, p53R270H in which arginine at position 270 of mouse p53 (at position 273 in the case of humans) is point-mutated to histidine, and p53D278N in which aspartic acid at position 278 of mouse p53 (at position 281 in the case of humans) is point-mutated to asparagine.

mRNA may be modified with pseudouridine ($\psi$) or 5-methyluridine (5 meU). mRNA may be polyadenylated.

RNA introduced into cells is, for example, single-stranded RNA, from which double-stranded RNA is substantially removed. In addition, RNA introduced into cells is preferably substantially free of impurities such as small RNA and contaminants. The single-stranded RNA introduced into cells may be purified and/or concentrated in order to substantially remove double-stranded RNA. Examples of methods for purifying single-stranded RNA introduced into cells include a purification method using high performance liquid chromatography (HPLC). For example, 70% or more, 75% or more, 80% or more, 85% or more, or 90% or more of double-stranded RNA is removed through HPLC. Alternatively, in order to substantially remove double-stranded RNA, RNA introduced into cells may be treated with ribonuclease that decomposes double-stranded RNA.

RNA introduced into cells may further include RNA in the transactivation domain (TAD) of MYOD that is directly connected to the full length of OCT3/4 RNA.

The reprogramming factor is introduced into cells, for example, by a lipofection method. The lipofection method is a method in which a complex of a nucleic acid, which is a negatively charged substance, and a positively charged lipid, is formed by an electrical interaction, and the complex is incorporated into cells by endocytosis or membrane fusion. The lipofection method has advantages such as less damage to cells, excellent introduction efficiency, ease of operation, and less time-consumption.

For example, the reprogramming factor is introduced into cells cultured using an RNA transfection reagent. For example, in the case where cells are mononuclear cells, immediately after mononuclear cells are isolated from blood, RNA may be introduced into mononuclear cells.

Lipofectamine MessengerMAX (registered trademark, Thermo Fisher SCIENTIFIC) can be used as the RNA transfection reagent. Alternatively, regarding the RNA transfection reagent, for example, a lipofection reagent such as Lipofectamine (registered trademark) RNAiMAX (Thermo Fisher SCIENTIFIC), Lipofectamine StemTransfection Reagent (Thermo Fisher SCIENTIFIC), TransIT (Mirus), mRNA-In (MTI-GlobalStem), Stemfect RNA Transfection Kit (ReproCELL), Jet Messenger (Polyplus), Lipofectamin (registered trademark) 2000, Lipofectamin (registered trademark) 3000, NeonTransfection System (Thermo Fisher SCIENTIFIC), Stemfect RNA transfection reagent (Stemfect), NextFect (registered trademark) RNA Transfection Reagent (BiooSientific), Amaxa (registered product) Human T cell Nucleofector (registered product) kit (Lonza, VAPA-1002), Amaxa (registered product) Human CD34 cell Nucleofector (registered product) kit (Lonza, VAPA-1003), and Repro-RNA (registered trademark) transfection reagent (STEMCELL Technologies) may be used.

Alternatively, for example, a reprogramming factor is introduced into cells using a viral vector. The viral vector may be an RNA viral vector. The RNA viral vector may be a Sendai virus vector. The Sendai virus vector may be a temperature-sensitive Sendai virus vector in which the stability of a viral nucleic acid decreases at a predetermined temperature or higher. The viral nucleic acid of the temperature-sensitive Sendai virus vector is stable below a predetermined temperature. The viral nucleic acid may be viral DNA or viral RNA. The viral nucleic acid may be a virus genome. The decrease in the stability of the viral nucleic acid may be at least one of decomposition of the viral nucleic acid and minimization of replication or proliferation of the viral nucleic acid. When the stability of the viral nucleic acid decreases, at least one of proliferation of the viral nucleic acid, the replication rate of the viral nucleic acid and the gene expression level decreases. The predetermined temperature is, for example, 36.5° C. or higher and 37.5° C. or lower, 36.6° C. or higher and 37.4° C. or lower, 36.7° C. or higher and 37.3° C. or lower, 36.8° C. or higher and 37.2° C. or lower, 36.9° C. or higher and 37.1° C. or lower, or 37° C. The stability of the viral nucleic acid of the temperature-sensitive Sendai virus vector, that is, at least one of the proliferation, the replication rate and the gene expression level, is high at a temperature lower than a predetermined temperature, and low at a predetermined temperature or higher. For example, in the temperature-sensitive Sendai virus vector, the proliferation rate or the gene expression level in cells cultured at 37° C. is ½ or less, ⅓ or less, ⅕ or less, 1/10 or less, or 1/20 or less with respect to the proliferation rate or the gene expression level in cells cultured at 32° C.

The Sendai virus encodes N gene, P gene, M gene, F/HN gene, and L gene. The HN protein recognizes sialic acid on the cell surface when the Sendai virus attaches to cells and fixes virus particles to the cells. The F protein is cleaved and activated with extracellular proteases, and catalyzes the fusion of the fixed Sendai virus envelope and the cell membrane of target cells to establish infection. Along with its modified protein, the P protein, the L protein catalyzes replication of viral nucleic acids in the cytoplasm after infection and transcription from the replicated multi-copy nucleic acids.

By deleting the F gene in the Sendai virus vector, it is possible to restrict production of infectious virus particles from transgenic cells. In addition, by introducing a mutation into at least one of the L gene and P gene, it is possible to make the Sendai virus vector temperature sensitive.

Examples of temperature-sensitive (TS) mutation of the Sendai virus include TS7 (Y942H/L1361C/L1558I mutation of the L protein), TS12 (D433A/R434A/K437A mutation of the P protein), TS13 (D433A/R434A/K437A mutation of the P protein and L1558I mutation of the L protein), TS14 (D433A/R434A/K437A mutation of the P protein and L1361C mutation of the L protein), and TS15 (D433A/R434A/K437A mutation of the P protein and L1361C/L1558I mutation of the L protein).

The Sendai virus vector is, for example, an F gene-deficient (ΔF) Sendai virus vector having G69E, T116A, and A183S mutations in the M protein, A262T, G264R, and K461G mutations in the HN protein, L511F mutation in the P protein, and N1197S and K1795E mutations in the L protein, which is a Sendai virus vector into which the TS7, TS12, TS13, TS14, or TS15 mutation is introduced. However, the temperature-sensitive mutation of the Sendai virus vector is not limited thereto.

The Sendai virus vector is, for example, SeV(PM)/TSΔF, SeV18+/TSΔF, or SeV(HNL)/TSΔF, and is a Sendai virus vector into which the TS7, TS12, TS13, TS14, or TS15 mutation is introduced. However, the temperature-sensitive mutation of the Sendai virus vector is not limited thereto.

The Sendai virus vector introduced into cells may be a combination of a temperature-sensitive Sendai virus vector and a temperature-insensitive Sendai virus vector. Alternatively, the Sendai virus vector introduced into cells may be a temperature-sensitive Sendai virus vector only and may not include a temperature-insensitive Sendai virus vector. For example, the Sendai virus vector introduced into cells may be only a temperature-sensitive Sendai virus vector into which the TS7, TS12, TS13, TS14, or TS15 mutation is introduced and may not include a temperature-insensitive Sendai virus vector. For example, the Sendai virus vector introduced into cells may be only a Sendai virus vector having a temperature sensitivity equal to or higher than that of a temperature-sensitive Sendai virus vector into which the TS7, TS12, TS13, TS14, or TS15 mutation is introduced, and may not include a temperature-insensitive Sendai virus vector. For example, the Sendai virus vector introduced into cells may be only a Sendai virus vector having a temperature sensitivity equal to higher than that of a temperature-sensitive Sendai virus vector into which the TS7, TS12, TS13, TS14, or TS15 mutation is introduced, and may not include a Sendai virus vector having a lower temperature sensitivity than a temperature-sensitive Sendai virus vector into which the TS7, TS12, TS13, TS14, or TS15 mutation is introduced.

The Sendai virus vector introduced into cells harbors arbitrary reprogramming factors. The Sendai virus vector introduced into cells may be, for example, a combination of a temperature-sensitive Sendai virus vector including KLF mRNA, OCT mRNA, and SOX mRNA in that order, and not including MYC mRNA, and a temperature-sensitive Sendai virus vector including MYC mRNA, and not including KLF mRNA, OCT mRNA, and SOX mRNA. However, the number, combination, and order of reprogramming factors harbored on the Sendai virus vector are arbitrary, and are not particularly limited.

The Sendai virus vector introduced into cells may include a Sendai virus vector including KLF mRNA and not including OCT mRNA and SOX mRNA. The Sendai virus vector including KLF mRNA and not including OCT mRNA and SOX mRNA may be a temperature-sensitive Sendai virus vector or a temperature-insensitive Sendai virus vector. However, according to the findings of the inventors, if a temperature-insensitive Sendai virus vector is not introduced, the Sendai virus vector disappears earlier from the cells into which the Sendai virus vector is introduced.

The temperature-sensitive Sendai virus vector including KLF mRNA, OCT mRNA, and SOX mRNA is, for example, an F gene-deficient Sendai virus vector having G69E, T116A, and A183S mutations in the M protein, A262T, G264R, and K461G mutations in the HN protein, L511F mutation in the P protein, and N1197S and K1795E mutations in the L protein, which is a Sendai virus vector including the TS7, TS12, TS13, TS14, or TS15 mutation. The temperature-sensitive mutation is, for example, TS7 or TS12, or TS12.

The temperature-sensitive Sendai virus vector including KLF mRNA, OCT mRNA, and SOX mRNA is, for example, SeV(PM)KOS/TS7ΔF or SeV(PM)KOS/TS12ΔF, or SeV (PM)KOS/TS12ΔF.

The temperature-sensitive Sendai virus vector including MYC mRNA is, for example, an F gene-deficient Sendai virus vector having G69E, T116A, and A183S mutations in the M protein, A262T, G264R, and K461G mutations in the HN protein, L511F mutation in the P protein, and N1197S and K1795E mutations in the L protein, which is a Sendai virus vector including the TS7, TS12, TS13, TS14, or TS15 mutation. The temperature-sensitive mutation is, for example, TS15.

The temperature-sensitive Sendai virus vector including MYC mRNA is, for example, SeV(HNL)MYC/TS12ΔF, SeV(HNL)MYC/TS13ΔF, or SeV(HNL)MYC/TS15ΔF.

The Sendai virus vector including KLF mRNA and not including OCT mRNA and SOX mRNA is, for example, an F gene-deficient Sendai virus vector having G69E, T116A, and A183S mutations in the M protein, A262T, G264R, and K461G mutations in the HN protein, L511F mutation in the P protein, and N1197S and K1795E mutations in the L protein. The Sendai virus vector including KLF mRNA and not including OCT mRNA and SOX mRNA is less temperature-sensitive than, for example, a Sendai virus vector into which the TS7, TS12, TS13, TS14, or TS15 mutation is introduced and can express the KLF gene at a predetermined temperature or higher.

The Sendai virus vector including KLF mRNA and not including OCT mRNA and SOX mRNA is, for example, SeV18+KLF4/TSΔF.

When a plurality of types of Sendai virus vectors are introduced into cells, for example, a plurality of types of Sendai virus vectors are introduced into cells at the same time. Alternatively, within 48 hours, within 36 hours, within 24 hours, within 18 hours, within 12 hours, within 10 hours, within 8 hours, within 6 hours, within 3 hours, within 2 hours, or within 1 hour after a certain type of Sendai virus vector is introduced into cells, it is preferable to introduce all types of Sendai virus vectors into cells.

The multiplicity of infection (MOI) of the Sendai virus vector when cells are infected is, for example, 0.1 or more, 0.3 or more, 0.5 or more, 1.0 or more, 2.0 or more, 3.0 or more, 4.0 or more, or 5.0 or more. In addition, the MOI is, for example, 100 or less, 90 or less, 80 or less, 70 or less, 60 or less, 50 or less, 40 or less, 30 or less, 20 or less, 10 or less, or 5 or less.

The temperature at which cells are infected with a Sendai virus vector may be lower than a predetermined temperature at which the stability of the viral nucleic acid of the temperature-sensitive Sendai virus vector decreases, that is, a temperature at which the viral nucleic acid of the temperature-sensitive Sendai virus vector is stable, or a predetermined temperature or higher. When the Sendai virus vector is only a temperature-sensitive Sendai virus vector and does not include a temperature-insensitive Sendai virus vector, the temperature at which cells are infected with a Sendai virus vector is preferably a temperature that is lower than a predetermined temperature at which the stability of the viral nucleic acid of the temperature-sensitive Sendai virus vector decreases, that is, a temperature at which the viral nucleic acid of the temperature-sensitive Sendai virus vector is stable.

The cells into which the reprogramming factor is introduced may be adherently cultured or suspension-cultured.

Somatic cells into which the reprogramming factor is introduced may be feeder-free cultured using a basement membrane matrix such as Matrigel (Corning), CELLstart (registered trademark, ThermoFisher), Laminin 511 (iMatrix-511, nippi), fibronectin, and vitrotin.

As the medium in which the cells into which the reprogramming factor is introduced are cultured, a stem cell medium such as a human ES/iPS medium, for example, Primate ES Cell Medium (ReproCELL), can be used.

However, the stem cell medium is not limited thereto and various stem cell mediums can be used. For example, Primate ES Cell Medium, Reprostem, ReproFF, ReproFF2, ReproXF (Reprocell), mTeSR1, TeSR2, TeSRE8, ReproTeSR (STEMCELL Technologies), PluriSTEM (registered trademark) Human ES/iPS Medium (Merck), NutriStem (registered trademark) XF/FF Culture Medium for Human iPS and ES Cells, Pluriton reprogramming medium (Stemgent), PluriSTEM (registered trademark), Stemfit AKO2N, Stemfit AK03 (Ajinomoto), ESC-Sure (registered trademark) serum and feeder free medium for hESC/iPS (Applied StemCell), L7 (registered trademark) hPSC Culture System (LONZA), and PluriQ (MTI-GlobalStem) may be used. The stem cell medium is put into a culture vessel, for example, a dish, a well, or a tube.

In the case where the cells are suspension-cultured or three-dimensionally cultured, for example, a gel medium is used. For example, the gel medium is prepared by adding gellan gum to a stem cell medium so that the final concentration is 0.001 mass % to 0.5 mass %, 0.005 mass % to 0.1 mass %, or 0.01 mass % to 0.05 mass %.

The gel medium may contain at least one polymer compound selected from the group consisting of gellan gum, hyaluronic acid, ramsan gum, diutan gum, xanthan gum, carrageenan, fucoidan, pectin, pectic acid, pectinic acid, heparan sulfate, heparin, heparitin sulfate, keratosulfate, chondroitin sulfate, dermatan sulfate, rhamnan sulfate, and salts thereof. In addition, the gel medium may contain methyl cellulose. When the gel medium contains methyl cellulose, aggregation between cells is further reduced.

Alternatively, the gel medium may contain a small amount of a temperature-sensitive gel selected from among poly(glycerol monomethacrylate) (PGMA), poly(2-hydroxypropyl methacrylate) (PHPMA), Poly(N-isopropylacrylamide) (PNIPAM), amine terminated, carboxylic acid terminated, maleimide terminated, N-hydroxysuccinimide (NHS) ester terminated, triethoxysilane terminated,
Poly(N-isopropylacrylamide-co-acrylamide),
Poly(N-isopropylacrylamide-co-acrylic acid),
Poly(N-isopropylacrylamide-co-butylacrylate),
Poly(N-isopropylacrylamide-co-methacrylic acid),
Poly(N-isopropylacrylamide-co-methacrylic acid-co-octadecyl acrylate), and N-Isopropylacrylamide.

The gel medium may or may not contain a growth factor, for example, a basic fibroblast growth factor (bFGF). Alternatively, the gel medium may contain a growth factor such as bFGF at a low concentration of 400 µg/L or less, 40 µg/L or less, or 10 µg/L or less.

In addition, the gel medium may or may not contain TGF-$\beta$, and may contain TGF-$\beta$ at a low concentration of 600 µg/L or less, 300 µg/L or less, or 100 µg/L or less.

The gel medium may not be stirred. In addition, the gel medium may not contain feeder cells.

The gel medium may contain at least one substance selected from the group consisting of cadherin, laminin, fibronectin, and vitronectin.

After the cells are infected with the Sendai virus vector, for at least 2 days, or 2 days or longer and 10 days or shorter, the cells may be cultured at a temperature lower than a predetermined temperature at which the stability of the viral nucleic acid of the temperature-sensitive Sendai virus vector decreases, that is, a temperature at which the viral nucleic acid of the temperature-sensitive Sendai virus vector is stable. Then, the cells may be cultured at a predetermined temperature or higher. While the cells are cultured at a predetermined temperature or higher, for example, the medium may be replaced once every two days.

After the cells are infected with the Sendai virus vector, the cells may be cultured for at least 2 days, or 2 days or longer and 10 days or shorter, for example, at a temperature of 4.0° C. or higher, 10° C. or higher, 15° C. or higher, 20° C. or higher, 25° C. or higher, 30° C. or higher, 31.0° C. or higher, 32.0° C. or higher, 33.0° C. or higher, 33.1° C. or higher, 33.2° C. or higher, 33.3° C. or higher, 33.4° C. or higher, 33.5° C. or higher, 33.6° C. or higher, 33.7° C. or higher, 33.8° C. or higher, or 33.9° C. or higher, lower than 37.0° C., lower than 36.9° C., lower than 36.8° C., lower than 36.7° C., lower than 36.6° C., lower than 36.5° C., 36.0° C. or lower, 35.0° C. or lower, or 34.0° C. or lower. Then, the temperature is raised, and the cells may be cultured at a temperature of 36.5° C. or higher, 36.6° C. or higher, 36.7° C. or higher, 36.8° C. or higher, 36.9° C. or higher, or 37.0° C. or higher, and 40.0° C. or lower, 39.0° C. or lower, or 38.0° C. or lower. The temperature may be raised once or stepwise. After the temperature is raised, while the cells are cultured, for example, the medium may be replaced once every two days.

After the cells are infected with the Sendai virus vector, until stem cell-like colonies begin to appear, the cells may be cultured at a temperature lower than a predetermined temperature at which the stability of the viral nucleic acid of the temperature-sensitive Sendai virus vector decreases, that is, a temperature at which the viral nucleic acid of the temperature-sensitive Sendai virus vector is stable. After the stem cell-like colonies begin to appear, the cells may be cultured at a predetermined temperature or higher. While the cells are cultured at a predetermined temperature or higher, for example, the medium may be replaced once every two days.

After the cells are infected with the Sendai virus vector, until stem cell-like colonies begin to appear, the cells may be cultured at a temperature of, for example, 4.0° C. or higher, 10° C. or higher, 15° C. or higher, 20° C. or higher, 25° C. or higher, 30° C. or higher, 31.0° C. or higher, 32.0° C. or higher, 33.0° C. or higher, 33.1° C. or higher, 33.2° C. or higher, 33.3° C. or higher, 33.4° C. or higher, 33.5° C. or higher, 33.6° C. or higher, 33.7° C. or higher, 33.8° C. or higher, or 33.9° C. or higher, and lower than 37.0° C., lower than 36.9° C., lower than 36.8° C., lower than 36.7° C., lower than 36.6° C., lower than 36.5° C., 36.0° C. or lower, 35.0° C. or lower, or 34.0° C. or lower. After the stem cell-like colonies begin to appear, the temperature is raised, and the cells may be cultured at a temperature of 36.5° C. or higher, 36.6° C. or higher, 36.7° C. or higher, 36.8° C. or higher, 36.9° C. or higher, or 37.0° C. or higher, and 40.0° C. or lower, 39.0° C. or lower, or 38.0° C. or lower. The temperature may be raised once or stepwise. After the temperature is raised, while the cells are cultured, for example, the medium may be replaced once every two days.

After the reprogramming factor is introduced into the cells and the cells are cultured, all cells into which the reprogramming factor is introduced are recovered, and at least part of the recovered and mixed cells are seeded and passaged in a medium, which is performed at least once. Then, all cells into which the reprogramming factor is introduced are recovered, and at least part of the recovered and mixed cells are seeded and passaged in a medium, which is performed a plurality of times. Until stem cells are generated, all cells into which the reprogramming factor is introduced may be recovered, and at least part of the recovered and mixed cells may be seeded and passaged in a medium. Here, all the recovered and mixed cells may be seeded in a medium.

Here, recovering the all cells into which the reprogramming factor is introduced and seeding and passaging at least part of the recovered and mixed cells in the medium refers to, for example, passaging the cells into which the reprogramming factor is introduced without distinguishing them according to the gene expression state. For example, during passage, the cells into which the reprogramming factor is introduced may be seeded in the same culture vessel without distinguishing them according to the gene expression state. Alternatively, recovering the all cells into which the reprogramming factor is introduced and seeding and passaging at least part of the recovered and mixed cells in a medium refers to, for example, passaging the cells into which the reprogramming factor is introduced without distinguishing them according to the degree of reprogramming. For example, during passage, the cells into which the reprogramming factor is introduced may be seeded in the same culture vessel without distinguishing them according to the degree of reprogramming.

Alternatively, recovering the all cells into which the reprogramming factor is introduced and seeding and passaging at least part of the recovered and mixed cells in the medium refers to, for example, passaging the cells into which the reprogramming factor is introduced without distinguishing them according to the morphology. For example, during passage, cells into which the reprogramming factor is introduced may be seeded in the same culture vessel without distinguishing them according to the morphology. Alternatively, recovering the all cells into which the reprogramming factor is introduced and seeding and passaging at least part of the recovered and mixed cells in the medium refers to, for example, passaging the cells into which the reprogramming factor is introduced without distinguishing the size. For example, during passage, the cells into which the reprogramming factor is introduced may be seeded in the same culture vessel without distinguishing the size.

In addition, alternatively, recovering the all cells into which the reprogramming factor is introduced and seeding and passaging at least part of the recovered and mixed cells in the medium refers to passaging without cloning the cells into which the reprogramming factor is introduced. For example, when passaging is performed without cloning, it is not necessary to pick up colonies formed by the cells into which the reprogramming factor is introduced. For example, when passaging is performed without cloning, a plurality of colonies formed by the cells into which the reprogramming factor is introduced may not be isolated from each other. For example, during passage, cells forming a plurality of different colonies may be mixed and seeded in the same culture vessel. In addition, for example, when passaging is performed without cloning, it is not necessary to clone a single colony formed by the cells into which the reprogramming factor is introduced. For example, during passage, colonies may be mixed and seeded in the same culture vessel.

For example, when the cells into which the reprogramming factor is introduced are adherently cultured, all cells that are adherently cultured may be recovered, and at least part of the recovered and mixed cells may be seeded and passaged in a medium. For example, during passage, all cells may be separated from the culture vessel, and at least part of the separated and mixed cells may be seeded in the same culture vessel. For example, all cells may be separated from the culture vessel with a separation solution and all separated and mixed cells may be passaged. For example, cells that do not form colonies may be passaged. When the cells into which the reprogramming factor is introduced are suspension-cultured, all suspension-cultured cells may be passaged.

When the cells into which the reprogramming factor is introduced are passaged, the cells are seeded in a medium or culture vessel at a low concentration. Here, the low concentration is, for example, 1 cell/cm$^2$ or more, $0.25 \times 10^4$ cells/cm$^2$ or less, $1.25 \times 10^3$ cells/cm or less, $0.25 \times 10^3$ cells/cm$^2$ or less, $0.25 \times 10^2$ cells/cm$^2$ or less, or $0.25 \times 10^1$ cells/cm$^2$ or less. Alternatively, the low concentration is a concentration at which 10 cells or less, 9 cells or less, 8 cells or less, 7 cells or less, 6 cells or less, 5 cells or less, 4 cells or less, 3 cells or less, or 2 cells or less can come into contact with each other and 11 cells or more do not come into contact with each other. Here, there may be a plurality of cell masses in which 10 cells or less come into contact with each other. Alternatively, the state in which the entire bottom surface of the cell container is covered with cells is regarded as 100% confluence, and the low concentration is 5% or less confluence, 4% or less confluence, 3% or less confluence, 2% or less confluence, 1% or less confluence, 0.5% or less confluence, 0.1% or less confluence, 0.05% or less confluence, or 0.01% or less confluence. In addition, alternatively, the low concentration is, for example, a concentration at which single cells do not come into contact with each other in the seeded cells. For example, single cells may be seeded in wells of a well plate. The well plate may be a 12-well plate or a 96-well plate. According to the findings of the inventors, when the cells into which the reprogramming factor is introduced are passaged, by seeding the cells in a medium at a low concentration, the residual Sendai virus in pluripotent stem cells induced from the cells can be minimized. The proportion of cells in which the Sendai virus remains among the induced pluripotent stem cells is, for example, 4% or less, 3% or less, 2% or less, 1% or less, 0.5% or less, or 0%.

When the temperature-sensitive Sendai virus vector is used, after passage, the cells may be cultured at a predetermined temperature or higher at which the stability of the viral nucleic acid of the temperature-sensitive Sendai virus vector decreases. After passage, for example, the cells may be cultured at a temperature of 36.5° C. or higher and lower than 38.0° C. After passage, for example, the cells are cultured at a temperature of 36.5° C. or higher and lower than 38.0° C. until intercellular adhesion starts, and after intercellular adhesion starts, until intercellular adhesion starts, the cells may be cultured at a higher temperature, for example, at a temperature of 37.5° C. or higher, 42.0° C. or lower, 41.5° C. or lower, 41.0° C. or lower, 40.5° C. or lower, or 40.0° C. or lower. After passage, before intercellular adhesion starts, the cells may be cultured at a temperature of 37.5° C. or higher, 42.0° C. or lower, 41.5° C. or lower, 41.0° C. or lower, 40.5° C. or lower, or 40.0° C. or lower.

The cells into which the reprogramming factor is introduced may be cultured and passaged in a closed culture vessel. In the closed culture vessel, for example, gases, viruses, microorganisms and impurities are not exchanged with the outside. In addition, the cells into which the reprogramming factor is introduced may be cultured and expanded in two-dimensional culture or may be cultured and expanded in three-dimensional culture.

After pluripotent stem cells are induced from the cells into which the reprogramming factor is introduced and the pluripotent stem cells are generated, all adherently cultured cells may be cryopreserved as pluripotent stem cells. For example, all cells separated from the culture vessel with a separation solution may be cryopreserved as pluripotent stem cells. In addition, after the pluripotent stem cells are induced from the cells into which the reprogramming factor is introduced, all suspension-cultured cells may be cryopreserved as pluripotent stem cells.

The induced pluripotent stem cells may form flat colonies similar to ES cells and express alkaline phosphatase. The induced pluripotent stem cells may express undifferentiated cell markers Nanog, OCT4, SOX2 and the like. The induced pluripotent stem cells may express TERT. The induced pluripotent stem cells may exhibit telomerase activity.

In addition, determination as to whether pluripotent stem cells are induced from the cells may be performed by analyzing whether at least one surface marker selected from among cell surface markers TRA-1-60, TRA-1-81, SSEA-1, and SSEA5 which indicate undifferentiation, with a flow cytometer, is positive. TRA-1-60 is an antigen specific for iPS/ES cells. Since iPS cells can be produced only from TRA-1-60 positive fractions, TRA-1-60 positive cells are considered to be the species of iPS cells.

Somatic cells in a state different from the state of the pluripotent stem cells may be induced from the induced pluripotent stem cells. Examples of the somatic cells include nerve cells, omental epithelial cells, hepatocytes, β cells, kidney cells, dental pulp stem cells, mesenchymal stem cells, somatic prestem cells, keratinocytes, dermal papilla cells, oral epithelial cells, cartilage cells, muscle cells, vascular cells, epithelial cells, cardiomyocytes, blood cells, and immune cells. Examples of blood cells include erythroblasts, red blood cells, megakaryocytes, and platelets. Examples of immune cells include monocytes, neutrophils, eosinophils, basophils, B cells, T cells, NK cells, and NKT cells. The induced stem cells may be differentiated into the endoderm, the mesoderm, or the ectoderm. Stem cells may form embryoid bodies, organoids, and spheres.

Examples of factors that induce nervous system cells from the cells include ASCL family, DLX family, MYT family, NeuroD family, SOX family, and NGN family. Examples of ASCL family include ASCL1. Examples of DLX family include DLX2. Examples of MYT family include MYT1L. Examples of NGN family include NGN2. Examples of nervous system cells include nerve cells, neural stem cells and neural progenitor cells. Examples of the nerve cells include inhibitory nerve cells, excitatory nerve cells, dopamin-producing nerve cells, cranial nerves, intervening nerves, and optic nerves. Alternatively, the nervous system cells may be motor nerve cells, oligodendrocyte progenitor cells, astrocytes, oligodendrocytes or the like.

Examples of factors that induce cardiomyocytes from the cells include GATA family, MEF family, TBX family, MYOCD family, MESP family, and miR-133 family. Examples of GATA family include GATA4A. Examples of MEF family include MEF2C. Examples of TBX family include TBX5. Examples of MESP family include MESP1.

Here, in the present disclosure, induction refers to reprogramming, initialization, transformation, transdifferentiation (Transdifferentiation or Lineage reprogramming), differentiation induction, cell fate change (Cell fate reprogramming) or the like.

After the generated pluripotent stem cells are treated so that somatic cells different from the pluripotent stem cells are induced from them, the induced cells may be cloned.

After the generated pluripotent stem cells are subjected to a gene editing treatment, gene-edited cells may be cloned.

Here, without passaging any cells into which the reprogramming factor is introduced, somatic cells different from the pluripotent stem cells may be induced from the cells into which the reprogramming factor is introduced. A method for introducing a reprogramming factor into cells is as described above. For example, without passaging any cells into which the reprogramming factor is introduced, a differentiation-inducing factor may be introduced into the cells into which the reprogramming factor is introduced, and somatic cells different from the pluripotent stem cells may be induced from the cells into which the reprogramming factor is introduced. Alternatively, without passaging any cells into which the reprogramming factor is introduced, a hormone or chemical substance may be applied to the cells into which the reprogramming factor is introduced, and somatic cells different from the pluripotent stem cells may be induced from the cells into which the reprogramming factor is introduced. In this case, the somatic cells are induced from the cells into which the reprogramming factor is introduced without being cloned. The induced somatic cells are as described above.

EXAMPLES

Example 1 and Comparative Example 1

A dish coated with laminin 511 was used as a dish for inducing pluripotent stem cells. In addition, human peripheral blood mononuclear cells were suspended in a blood medium, the number of mononuclear cells was measured using a blood cell counting chamber, and the number of mononuclear cells in the blood medium was adjusted. Then, the mononuclear cells were two-dimensionally cultured on the dish for inducing pluripotent stem cells at 37° C. for 1 to 7 days.

SeV(PM)hKOS/TS12ΔF and SeV(HNL)hC-Myc/TS15ΔF were added to the two-dimensionally cultured mononuclear cells so that the MOI was 5, the dish for inducing pluripotent stem cells was accommodated in an incubator at 34° C., and the cells were cultured. Two days after infection, the blood medium was replaced with an iPS cell medium. Then, the medium was replaced once every two days using the iPS cell medium. Along the way, the temperature was gradually raised to 37° C., 38° C.

8 days after infection, stem cell-like cell masses were generated. On the 14th day after infection, almost all cells become TRA1-60 positive cells, and showed iPS cell-like morphology. 14 days after infection, a triple select as a cell-releasing agent was added to the dish and left at room temperature for 1 minute, and a cell-containing solution was then sucked up, and the cell-containing solution was incubated at 37° C. for 5 minutes to 10 minutes. Then, an iPS cell medium was added, and the cell-containing iPS cell medium was recovered in a 15 mL tube. The number of cells was measured using a blood cell counting chamber, the concentration of the cell-containing solution was adjusted, the cells were seeded in the well plate so that the concentration was $0.25 \times 10^4$ cells/cm$^2$ or less, and the first passage was performed. In Example 1, during the first passage, all cells were separated from the well plate, and the separated and mixed cells were seeded in the next well plate without distinguishing. On the other hand, in Comparative Example 1, during the first passage, colonies were picked and cloned. Here, in both Example 1 and Comparative Example 1, during passage, cells were seeded so that 11 or more cells did not come into contact with each other.

Next, the well-dish was accommodated in an incubator at 37° C., and cells were two-dimensionally cultured. After the cells began to divide, the culture temperature was raised to 38° C. Thereafter, in both Example 1 and Comparative Example 1, all cells were recovered each time the cells had 60% to 80% confluence, and at least part of the recovered and mixed cells were seeded and passaged in a medium. From the second passage onward, the cells were seeded in the well plate so that the concentration was $0.25 \times 10^4$ cells/cm$^2$ or less. In this case also, 11 or more cells did not come into contact with each other.

Figure 1B:
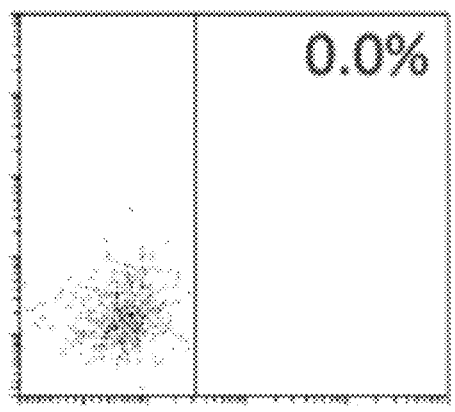
Figure 2:
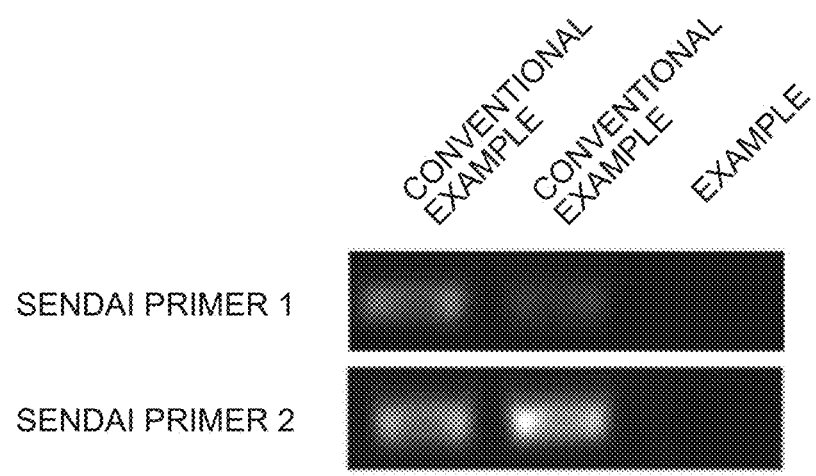
FIG. 2 is a graph showing PCR results according to Example 1.
Figure 3A:
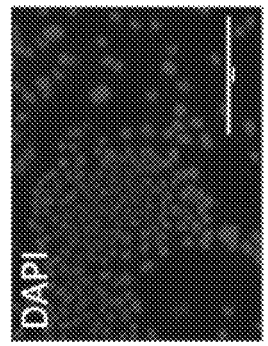
FIGS. 3A to 3C shows images of TRA1-60 positive cells according to Example 1.
Figure 3B:
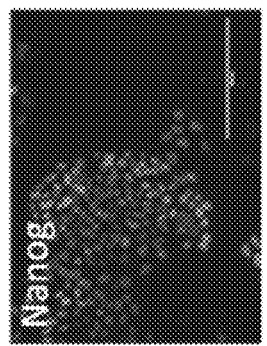
Figure 3C:
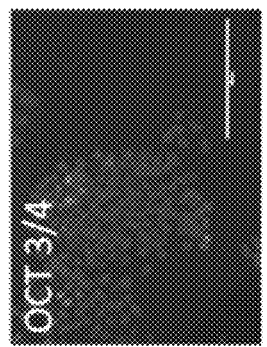

As shown in FIGS. 1A and 1B, when the cells that had been passaged only once were stained with anti-Sendai virus antibodies and the Sendai virus remaining in the cells according to Example 1 was evaluated with a flow cytometer, the Sendai virus in the cells disappeared. As shown in FIG. 2, the Sendai virus remaining in the cells according to Example 1 was not detected by PCR. As in the prior art, when cells were seeded at a high concentration at which 11 or more cells were adhered to each other, the Sendai virus remained in the cells. FIGS. 3A to 3C shows immunostaining images of the obtained TRA1-60 positive cells.

In addition, the number of colonies formed 5 days after the Sendai virus in the cells disappeared was counted. In addition, the clonal efficiency was calculated by dividing the number of colonies by the number of seeded cells. FIGS. 4A and 4B shows the results of three experiments. When all cells were recovered using mTeSR Plus as a medium during the first passage, and part of the recovered and mixed cells were seeded and passaged in the medium, the clonal efficiency was about 5% to about 8%, with a small variation. When colonies were picked and cloned using mTeSR Plus as a medium during the first passage, the clonal efficiency may be less than 1% or about 6%, there was a variation in the clonal efficiency. When all cells were recovered using Stem-Fit as a medium during the first passage, and part of the recovered and mixed cells were seeded and passaged in the medium, the clonal efficiency was about 10% to about 15%, with a small variation. When colonies were picked and cloned using StemFit as a medium during the first passage, the clonal efficiency was less than 1% or about 16%, there was a variation in the clonal efficiency.

Therefore, it was shown that, when all cells into which the reprogramming factors were introduced were recovered during the first passage and at least part of the recovered and mixed cells were seeded and passaged in a medium, the clonal efficiency was high and stable.

Example 2 and Comparative Example 2

Figure 5:
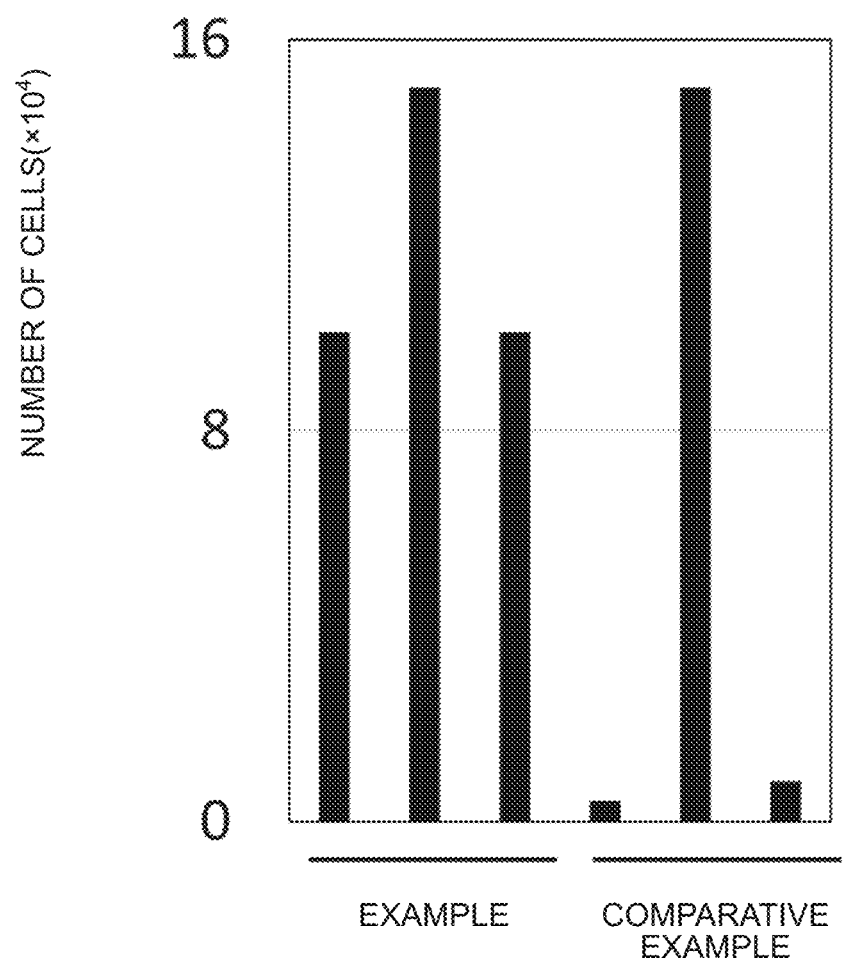
FIG. 5 is a graph showing the number of cells according to Example 2 and Comparative Example 2.
Figure 6:
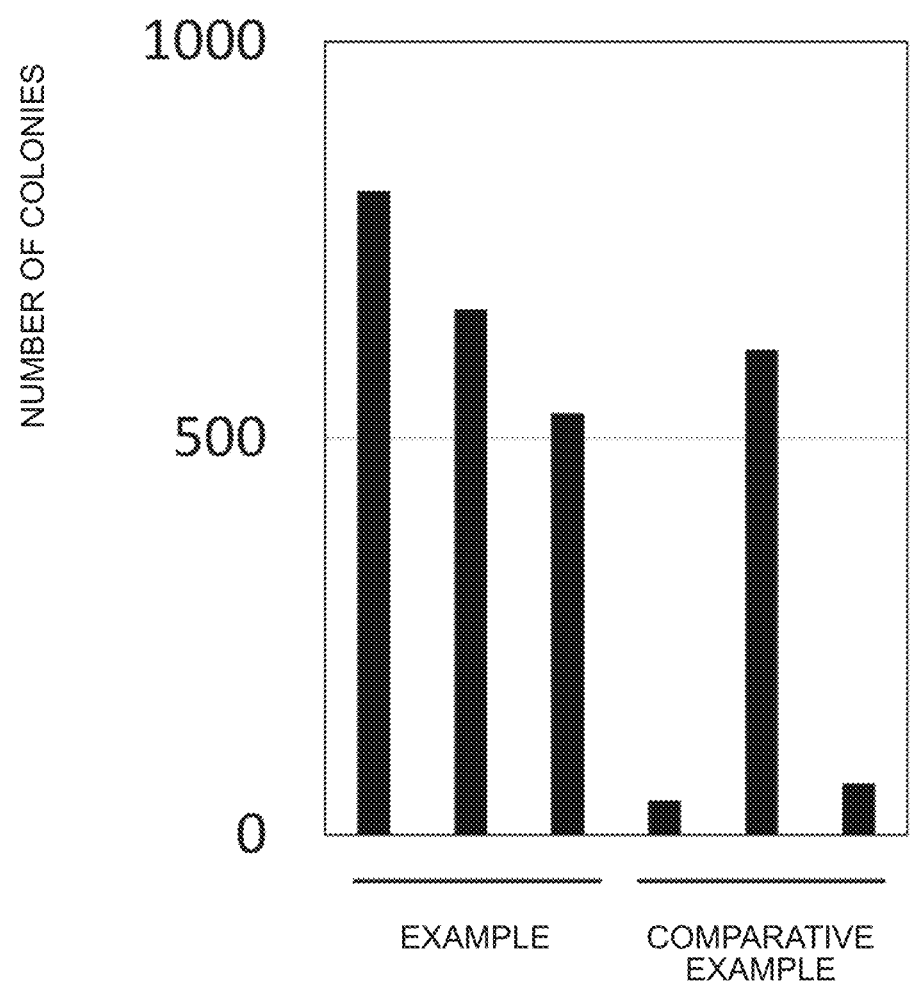
FIG. 6 is a graph showing the number of colonies according to Example 2 and Comparative Example 2.

The iPS cell-like cells obtained by passage in the same manner as in Example 1 and Comparative Example 1 were separated and dissociated. Next, about $1 \times 10^5$ cells were cryopreserved using STEM-CELLBANKER (registered trademark, Takara). Then, the frozen cells were thawed, about $1 \times 10^4$ cells were seeded in the well, and the cells were cultured and proliferated. The number of cells and the number of colonies 7 days after seeding were measured. FIG. 5 and FIG. 6 show the results of three experiments.

As shown in FIG. 5, when all cells were recovered and part of the recovered and mixed cells were seeded and passaged in a medium during the first passage, the number of cells cultured for 7 days after freezing and thawing was about $10 \times 10^4$ to about $15 \times 10^4$, with a small variation. On the other hand, in regard to cells cloned by picking colonies during the first passage, the number of cells cultured for 7 days after freezing and thawing was about $0.4 \times 10^4$ to about $15 \times 10^4$ cells, with a large variation. Therefore, it was shown that, when all cells into which the reprogramming factors were introduced were recovered during the first passage and at least part of the recovered and mixed cells were seeded and passaged in a medium, the proliferation rate of the cells after freezing and thawing was high and stable.

As shown in FIG. 6, when all cells were recovered during the first passage and at least part of the recovered and mixed cells were seeded and passaged in a medium, the number of colonies of cells cultured for 7 days after freezing and thawing was about 500 to about 800 colonies, with a small variation. On the other hand, in regard to cells cloned by picking colonies during the first passage, the number of colonies of cells cultured for 7 days after freezing and thawing was about 30 to about 600, with a large variation. Therefore, it was shown that, when all cells into which the reprogramming factors were introduced were recovered during the first passage and at least part of the recovered and mixed cells were seeded and passaged in a medium, the colony forming rate of cells after freezing and thawing was high and stable.

Figure 7:
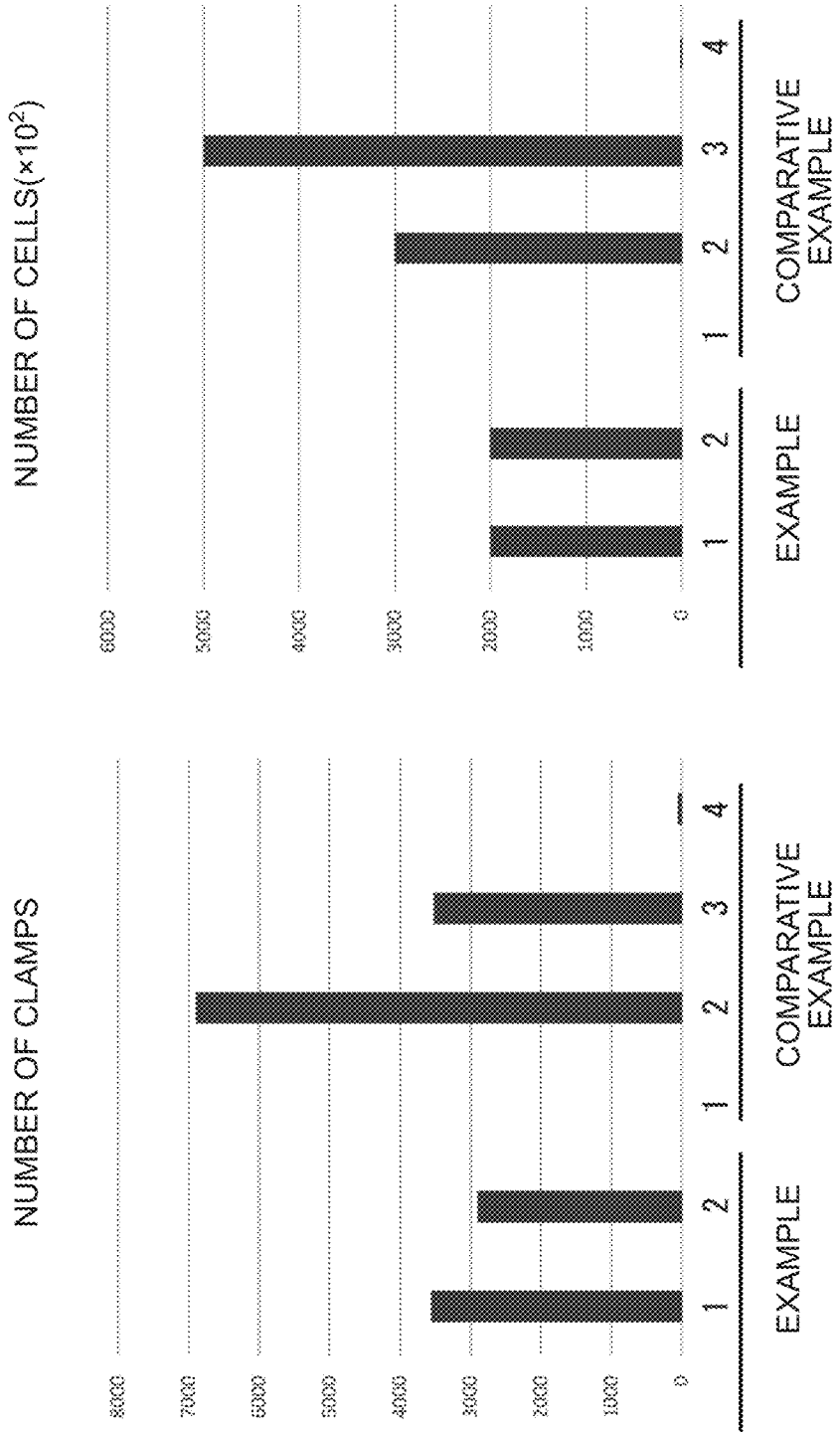
FIGS. 7A and 7B shows graphs of the number of clamps and the number of cells according to Example 3 and Comparative Example 3.

Example 3 and Comparative Example 3 iPS cell-like cells obtained by passage in the same manner as in Example 1 and Comparative Example 1 were separated, $2.5 \times 10^5$ cells were suspended in a gel medium, the cells were three-dimensionally cultured, and clamps were formed by the cells. The number of clamps and the number of cells 13 days after the cells were seeded in the gel medium were measured. FIGS. 7A and 7B shows the results obtained by testing the cells obtained in Example 1 twice and the cells obtained in Comparative Example 1 4 times.

When all cells were recovered during the first passage and part of the recovered and mixed cells were seeded and passaged in a medium, the cells were three-dimensionally cultured, about 3,000 clamps were formed, and the variation between experiments was small. In addition, when all cells were recovered during the first passage and part of the recovered and mixed cells were seeded and passaged in a medium, the cells were three-dimensionally cultured and about $2,000 \times 10^2$ cells were obtained, and the variation between experiments was small. On the other hand, in regard to cells cloned by picking colonies during the first passage, about 7,000 clamps were formed in some experiments, but cells died and formed almost no clamps in some experiments, and the variation between experiments was large. In addition, cells cloned by picking colonies during the first passage were three-dimensionally cultured and about 5,000×10² cells were obtained in some experiments, but cells died and the number of cells was almost 0 in some experiments, and the variation between experiments was large.

Therefore, it was shown that, when all cells into which the reprogramming factors were introduced were recovered during the first passage and at least part of the recovered and mixed cells were seeded and passaged in a medium, the proliferation rate and the clamp forming ability of cells in the subsequent three-dimensional culture were improved and stable.

Example 4 and Comparative Example 4 iPS cell-like cells obtained by passage in the same manner as in Example 1 and Comparative Example 1 were separated, and the iPS cell-like cells were differentiated into cardiomyocytes using a cardiomyocyte differentiation induction kit (PSC Cardiomyocyte Differentiation Kit, Gibco, registered trademark).

Specifically, in a 12-well plate whose bottom surface was treated with a basement membrane matrix (Corning Matrigel, registered trademark), about 2×10⁴ to about 6×10⁴ iPS cell-like cells were seeded, and the cells were cultured using mTeSR1 as a medium. Two days after iPS cell-like cells were seeded, the medium was replaced with a Cardiomyocyte Differentiation Medium A. Two days later, the medium was replaced with a Cardiomyocyte Differentiation Medium B. Two days later, the medium was replaced with a Cardiomyocyte Maintenance Medium. Then, every two days up to the 22$^{nd}$ day, the cells were cultured after the iPS cell-like cells were seeded while the medium was replaced with a Cardiomyocyte Maintenance Medium.

As a result, as shown in FIG. 8, the cells obtained by recovering the all cells during the first passage after the reprogramming factors were introduced and seeding and passaging part of the recovered and mixed cells in the medium before the cells were induced to differentiate into the cardiomyocytes showed pulsation on the 22$^{nd}$ day in all the experiments. On the other hand, the cells cloned by picking colonies during the first passage after the reprogramming factors were introduced and before the cells were induced to differentiate into the cardiomyocytes showed pulsation on the 22$^{nd}$ day only in less than half of the experiments.

Figure 9:
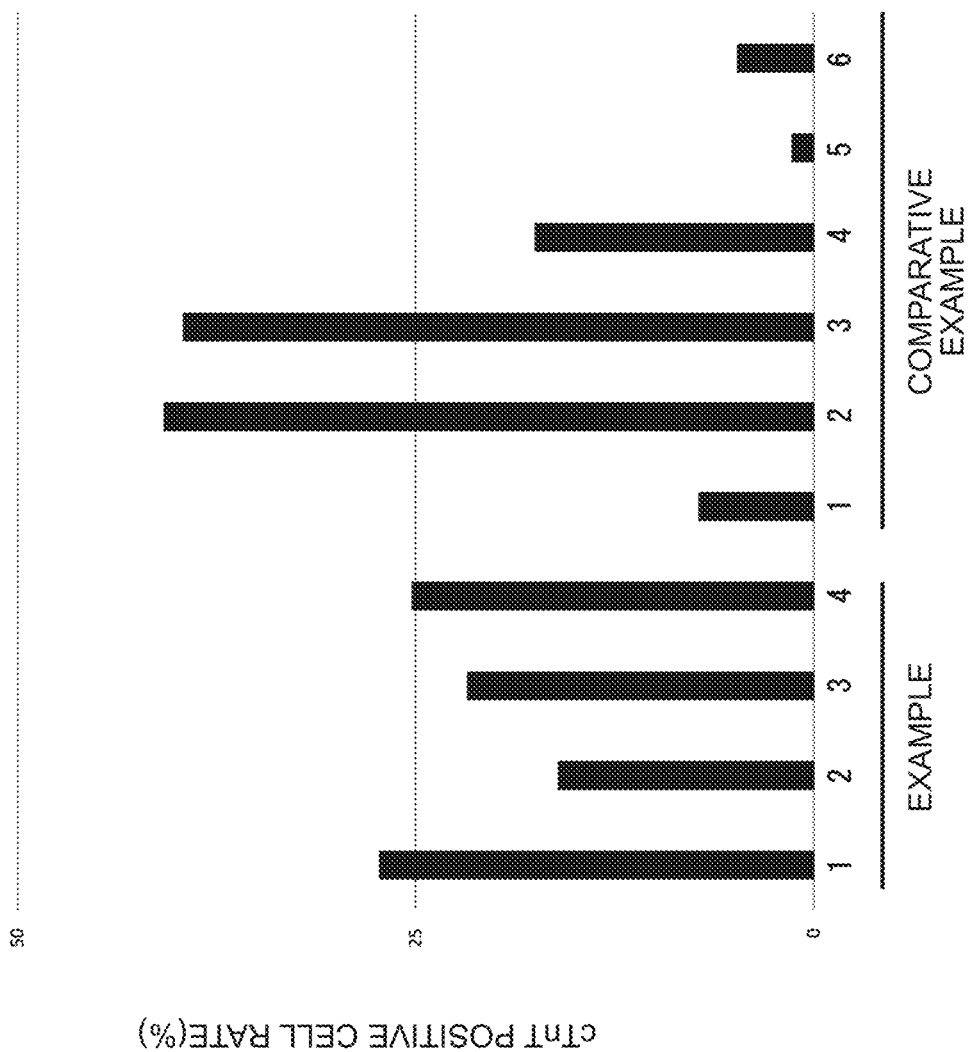
FIG. 9 is a graph showing the positive rate of cTnT according to Example 4 and Comparative Example 4.

In addition, when the positive rate of cardiac troponin T(cTnT), which is a marker of cardiomyocytes, was examined by FACS, as shown in FIG. 9, the cells obtained by recovering the all cells during the first passage and seeding and passaging part of the recovered and mixed cells in the medium after the reprogramming factors were introduced and before the cells were induced to differentiate into the cardiomyocytes were stable with a cTnT positive rate of around 20%. On the other hand, the cells cloned by picking colonies during the first passage after the reprogramming factors were introduced and before the cells were induced to differentiate into the cardiomyocytes had a large variation in the cTnT positive rate of about 1% to about 37%.

Therefore, it was shown that, when all cells into which the reprogramming factors were introduced were recovered during the first passage, at least part of the recovered and mixed cells were seeded and passaged in a medium, and stem cells were generated, an ability to induce differentiation into somatic cells such as cardiomyocytes was high and stable thereafter.

Example 5 and Comparative Example 5

The iPS cell-like cells obtained by passage in the same manner as in Example 1 and Comparative Example 1 were separated, and 1.5×10⁵ cells were seeded and cultured in a round-bottomed cell culture plate having a size suitable for cell mass formation (Kuraray, RB 500 400 NA 6).

For the medium, an 8 GMK medium (8% KnockOut Serum Replacement (Life Technologies)) to which ALK-4, -5, -7 selective inhibitor for TGF-β1 activin receptor-like kinase (ALK) (500 nmol/L, A-83-01, Stemgent) and a membrane permeable inhibitor (100 nmol/L, LDN193189, Stemgent) for BMP Type I receptor (ALK2, ALK3) were added, 1% non-essential amino acid (NEAA, Life Technologies), and 1% sodium pyruvate (Sigma), 100 nmol/L 2-mercaptoethanol (2-ME, Life Technologies) were used. It was known that pluripotent stem cells cultured in the presence of the above inhibitor were inducted to differentiate into neural progenitor cells.

Figure 10A:
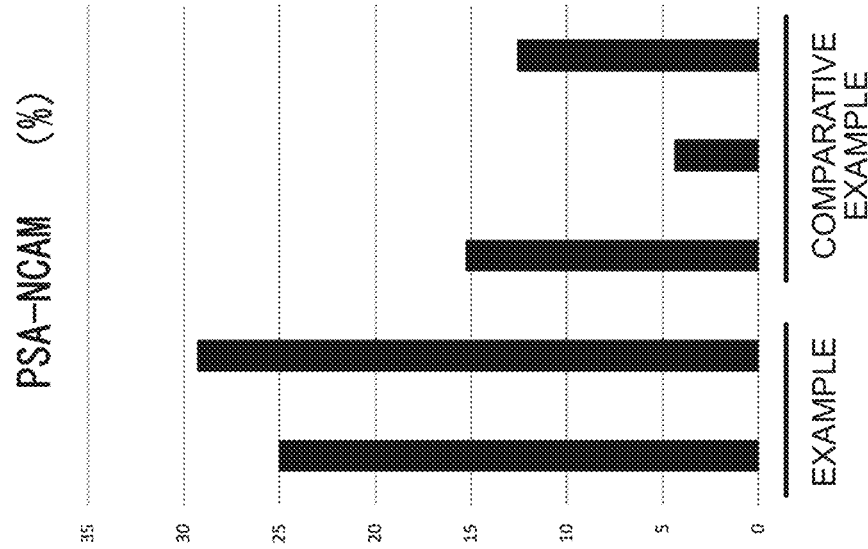
FIGS. 10A and 10B shows graphs of the number of cells and the positive rate of PSA-NCAM according to Example 5 and Comparative Example 5.
Figure 10B:
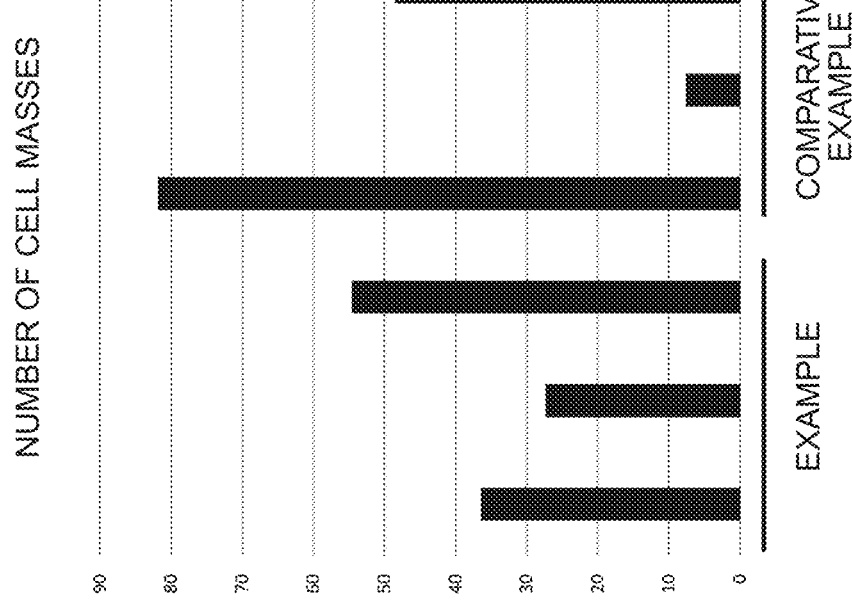
Figure 12A:
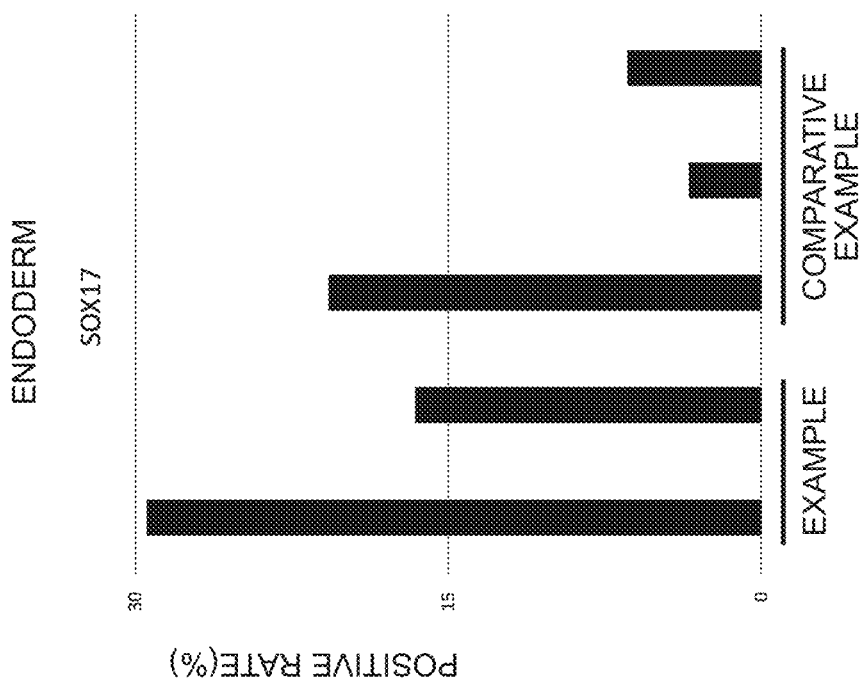
FIGS. 12A and 12B shows graphs of the positive rate of HAND1 and the positive rate of SOX17 according to Example 6 and Comparative Example 6.
Figure 12B:
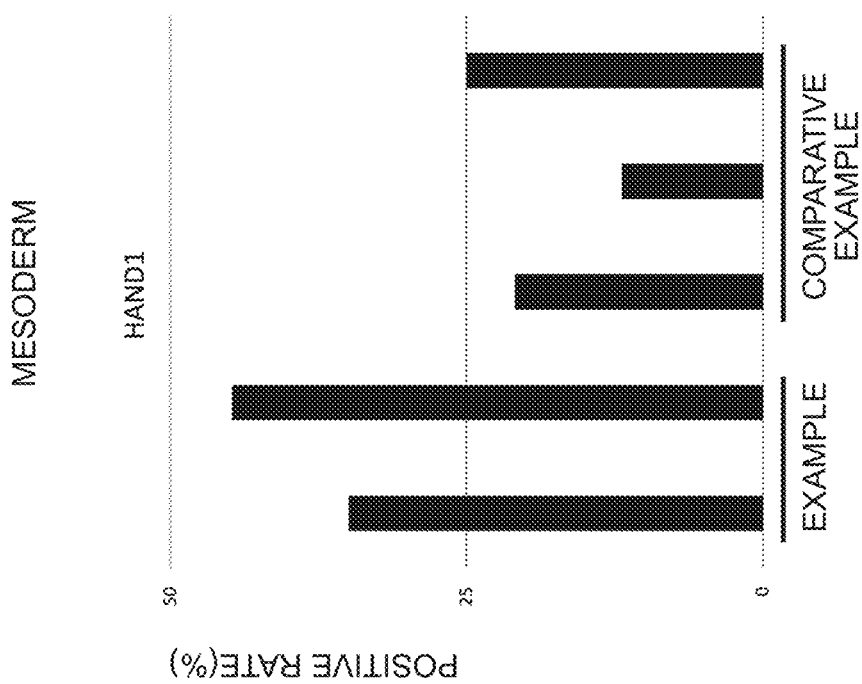

The medium was replaced 5 days, 8 days, and 11 days after the cells were seeded. After 14 days, when the number of cell masses was measured, as shown in FIGS. 10A and 10B, the cells obtained by recovering the all cells during the first passage and seeding and passaging at least part of the recovered and mixed cells in the medium after the reprogramming factors were introduced and before the cells were induced to differentiate into the neural progenitor cells formed about 25 to about 55 neurospheres, with a small variation. On the other hand, the cells cloned by picking colonies during the first passage after the reprogramming factors were introduced and before the cells were induced to differentiate into the neural progenitor cells formed about 10 to about 80 cell masses, with a large variation.

In addition, after 14 days, the cells were recovered in a tube and centrifuged, cell masses were dissociated into single cells with a cell dissociator (TrypLE Select, ThermoFisher, registered trademark), and the number of cells was measured, and the cells were then immunostained using PSA-NCAM antibodies which are antibodies that detect polysialization molecules of nerve cell adhesion molecules (N-CAM), and the positive rate of PSA-NCAM was analyzed by flow cytometry. As a result, as shown in FIGS. 10A and 10B, the cells obtained by recovering the all cells during the first passage and seeding and passaging at least part of the recovered and mixed cells in the medium after the reprogramming factors were introduced and before the cells were induced to differentiate into the neural progenitor cells had a positive rate of PSA-NCAM of about 25% to about 30%, with a small variation. On the other hand, the cells cloned by picking colonies during the first passage after the reprogramming factor were introduced and before the cells were induced to differentiate into the neural progenitor cells had a positive rate of PSA-NCAM of about 5% to about 15%, with a large variation.

Therefore, it was shown that, when all cells into which the reprogramming factors were introduced were recovered during the first passage, at least part of the recovered and mixed cells were seeded and passaged in a medium, and stem cells were generated, an ability to induce differentiation into somatic cells such as nerve cells was high and stable thereafter.

Example 6 and Comparative Example 6

The iPS cell-like cells obtained by passage in the same manner as in Example 1 and Comparative Example 1 were separated, and $1\times10^5$ cells were seeded and cultured in a non-adhesive dish. Regarding the medium, a human ES cell medium to which no bFGF was added was used. In addition, the medium was replaced once every two days. 9 days after seeding, the formed embryoid bodies (EB) were seeded again in a gelatin-coated 6-well plate. Then, the medium was replaced once every two days, and the cells were recovered by a trypsin treatment on the 24th day after seeding again. The recovered cells were immobilized with 4% paraformaldehyde, the cells were stained using SOX1 antibodies, OTC2 antibodies, HAND1 antibodies, and SOX17 antibodies, and the stained cells were analyzed using a flow cytometer. Here, SOX1 and OTX2 are ectoderm markers, HAND1 is a mesoderm marker, and SOX17 is an endoderm marker.

As a result, as shown in FIGS. 11A and 11B, and FIGS. 12A and 12B, the cells obtained by recovering the all during the first passage and seeding and passaging part of the recovered and mixed cells in the medium after the reprogramming factors were introduced had a small variation in the positive rate of each marker. On the other hand, the cells cloned by picking colonies during the first passage after the reprogramming factors were introduced had a large variation in the positive rate of each marker. Therefore, it was shown that, when all cells into which the reprogramming factor were introduced were recovered during the first passage and at least part of the recovered and mixed cells were seeded and passaged in a medium, an ability to differentiate into the endoderm, the mesoderm, and the ectoderm was high and stable thereafter.

Reference Example 1

SeV(PM)hKOS/TS12ΔF, SeV18+hKLF4/TSΔF, and SeV(HNL)hC-Myc/TS15ΔF were added to two-dimensionally cultured fibroblasts so that the MOI was 5, a dish for inducing pluripotent stem cells was accommodated in an incubator at 34° C., and the cells were cultured. Two days after infection, the blood medium was replaced with an iPS cell medium. Then, the medium was replaced once every two days using the iPS cell medium. On the $14^{th}$ day after infection, the culture temperature was gradually raised to 37° C. and 38° C.

10 days after infection, stem cell-like cell masses were generated. On the 14th day after infection, almost all cells become TRA1-60 positive cells, and showed iPS cell-like morphology. 14 days after infection, a triple select as a cell-releasing agent was added to the dish, and a cell-containing solution was incubated at 37° C. for 5 minutes to 10 minutes. Then, an iPS cell medium was added, and the cell-containing iPS cell medium was recovered in a 15 mL tube. The number of cells was measured using a blood cell counting chamber, the concentration of the cell-containing solution was adjusted, the cells were seeded in the well plate so that the concentration was $0.25\times10^4$ cells/cm$^2$ or less, and the first passage was performed. In this case, 11 or more cells did not come into contact with each other. Next, the well-dish was accommodated in an incubator, and the cells were two-dimensionally cultured. After the cells began to divide, the culture temperature was set to 38° C. Then, the cells were passaged so that the cells had 60% to 80% confluence. From the second passage onward, the cells were seeded in the well plate so that the concentration was $0.25\times10^4$ cells/cm$^2$ or less. In this case also, 11 or more cells did not come into contact with each other.

Figure 13B:
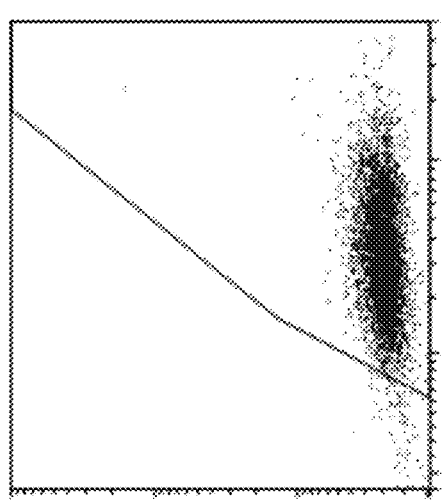
FIGS. 13A and 13B shows graphs of the measurement results obtained by a flow cytometer according to Reference Example 1.
Figure 13A:
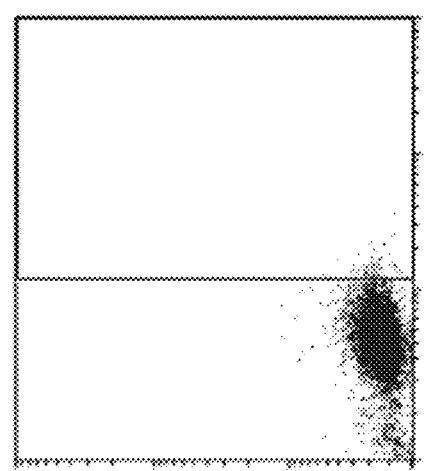
Figure 14:
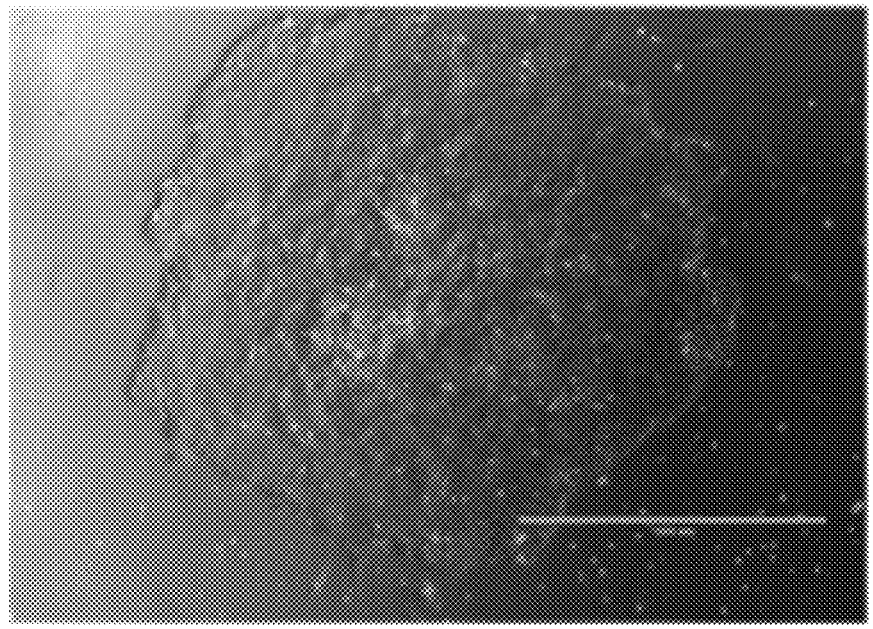
FIG. 14 is an image showing TRA1-60 positive cells according to Reference Example 1.

As shown in FIGS. 13A and 13B, when the cells that had been passaged only once were stained with anti-Sendai virus antibodies and the Sendai virus remaining in the cells was evaluated with a flow cytometer, the Sendai virus in the cells was almost disappeared. FIG. 14 shows an image of the obtained TRA1-60 positive cells.

Reference Example 2

SeV(PM)hKOS/TS12ΔF, SeV18+hKLF4/TSΔF, and SeV(HNL)hC-Myc/TS15ΔF were added to two-dimensionally cultured mononuclear cells so that the MOI was 5, a dish for inducing pluripotent stem cells was accommodated in an incubator at 37° C. and the cells were cultured. Two days after infection, the blood medium was replaced with an iPS cell medium. Then, the medium was replaced once every two days using the iPS cell medium.

8 days after infection, stem cell-like cell masses were generated. 14 days after infection, a triple select as a cell-releasing agent was added to the dish and left at room temperature for 1 minute, and a cell-containing solution was then sucked up, and the cell-containing solution was incubated at 37° C. for 5 minutes to 10 minutes. Then, an iPS cell medium was added, and the cell-containing iPS cell medium was recovered in a 15 mL tube. The concentration of the cell-containing solution was adjusted so that 11 or more cells adhered to each other, and the cells were seeded in a well plate for the first passage so that the concentration was higher than $0.25\times10^4$ cells/cm$^2$. Next, the well-dish was accommodated in an incubator at 37° C., and the cells were two-dimensionally cultured. After the cells began to divide, the culture temperature was raised to 38° C. Then, the cells were passaged so that the cells had 60% to 80% confluence. From the second passage to the fifth passage, 11 or more cells adhered to each other, and the cells were seeded in a well plate so that the concentration was higher than $0.25\times10^4$ cells/cm$^2$. From the sixth passage onward, the cells were seeded in a well plate so that the concentration was $0.25\times10^4$ cells/cm$^2$ or less. In this case, 11 or more cells did not come into contact with each other.

As shown in FIGS. 15A to 15G, when the cells were stained using anti-Sendai virus antibodies and the Sendai virus remaining in the cells was evaluated with a flow cytometer, the Sendai virus remained in the cells before the sixth passage. However, after the sixth passage in which the cells were seeded in a well plate so that the concentration was $0.25\times10^4$ cells/cm$^2$ or less, the Sendai virus in the cells rapidly disappeared.

Reference Example 3

CytoTune-iPS2.0 (registered trademark, ID Pharma), which is a Sendai virus vector kit, was prepared. CytoTune-iPS2.0 includes SeV(PM)hKOS/TS12ΔF, which is a temperature-sensitive Sendai virus vector that carries KLF4 genes, OCT3/4 genes, and SOX2 genes as reprogramming factors, SeV18+hKLF4/TSΔF, which is a temperature-sensitive Sendai virus vector that carries KLF4 as a reprogramming factor, and SeV(HNL)hC-Myc/TS15ΔF, which is a temperature-sensitive Sendai virus vector that carries c-MYC as a reprogramming factor.

SeV(PM)hKOS/TS12ΔF, SeV18+hKLF4/TSΔF, and SeV(HNL)hC-Myc/TS15ΔF were added to mononuclear cells so that the MOI was 5, and a dish for inducing pluripotent stem cells was accommodated in an incubator at 37° C. and the cells were cultured. Two days after infection, the blood medium was replaced with an iPS cell medium (mTeSR Plus (STEMCELL Technologies) or StemFit (Ajinomoto)). Then, the medium was replaced once every two days using the iPS cell medium.

8 days after infection, stem cell-like cell masses were generated. On the 14th day after infection, almost all cells become TRA1-60 positive cells, and showed iPS cell-like morphology. 14 days after infection, a triple select as a cell-releasing agent was added to the dish and left at room temperature for 1 minute, and a cell-containing solution was then sucked up, and the cell-containing solution was incubated at 37° C. for 5 minutes to 10 minutes. Then, an iPS cell medium was added, and the cell-containing iPS cell medium was recovered in a 15 mL tube. The number of cells was measured using a blood cell counting chamber, the concentration of the cell-containing solution was adjusted, the cells were seeded in the well plate so that the concentration was $0.25 \times 10^4$ cells/cm$^2$ or less, and the first passage was performed. In this case, 11 or more cells did not come into contact with each other.

Next, the well-dish was accommodated in an incubator at 37° C., and the cells were two-dimensionally cultured. Then, the cells were passaged so that the cells had 60% to 80% confluence. From the second passage onward, the cells were seeded in the well plate so that the concentration was $0.25 \times 10^4$ cells/cm$^2$ or less. In this case also, 11 or more cells did not come into contact with each other.

Figure 16A:
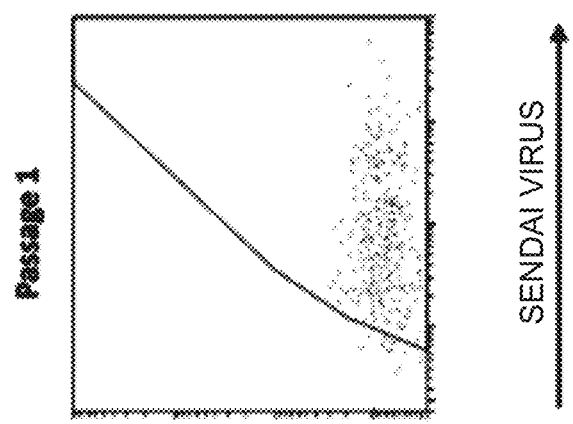
FIGS. 16A to 16C shows graphs of the measurement results obtained by a flow cytometer according to Reference Example 3.
Figure 16B:
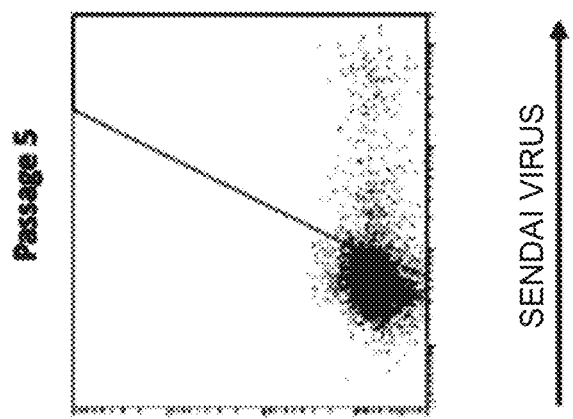
Figure 16C:
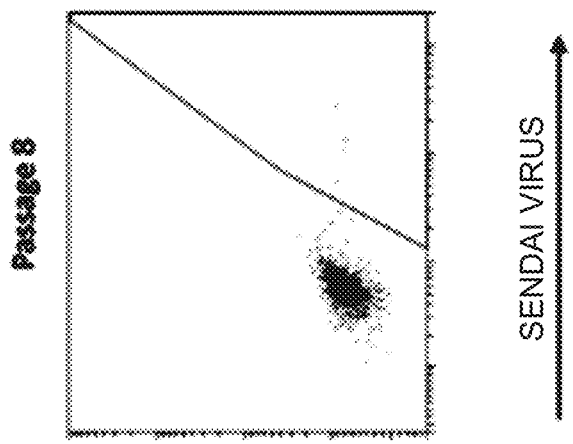

As shown in FIGS. 16A to 16C, when the cells were stained using anti-Sendai virus antibodies and the Sendai virus remaining in the cells was evaluated with a flow cytometer, at the 8th passage, the Sendai virus in the cells almost disappeared.

Reference Example 4

SeV(PM)hKOS/TS12ΔF and SeV(HNL)hC-Myc/TS15ΔF were added to the two-dimensionally cultured mononuclear cells so that the MOI was 5, the dish for inducing pluripotent stem cells was accommodated in an incubator at 34° C., and the cells were cultured. Two days after infection, the blood medium was replaced with an iPS cell medium. Then, the medium was replaced once every two days using the iPS cell medium. Along the way, the temperature was raised to 38° C.

8 days after infection, stem cell-like cell masses were generated. On the 14th day after infection, almost all cells become TRA1-60 positive cells, and showed iPS cell-like morphology. 15 days after infection, a triple select as a cell-releasing agent was added to the dish and left at room temperature for 1 minute, and a cell-containing solution was then sucked up, and the cell-containing solution was incubated at 37° C. for 5 minutes to 10 minutes. Then, an iPS cell medium was added, and the cell-containing iPS cell medium was recovered in a 15 mL tube. The number of cells was measured using a blood cell counting chamber, the concentration of the cell-containing solution was adjusted, the cells were seeded in the well plate so that the concentration was $0.25 \times 10^4$ cells/cm$^2$ or less, and the first passage was performed. In this case, 11 or more cells did not come into contact with each other. Next, the well-dish was accommodated in an incubator at 38° C., and the cells were two-dimensionally cultured. Then, the cells were passaged so that the cells had 60% to 80% confluence. From the second passage onward, the cells were seeded in the well plate so that the concentration was $0.25 \times 10^4$ cells/cm$^2$ or less. In this case also, 11 or more cells did not come into contact with each other.

Figure 17A:
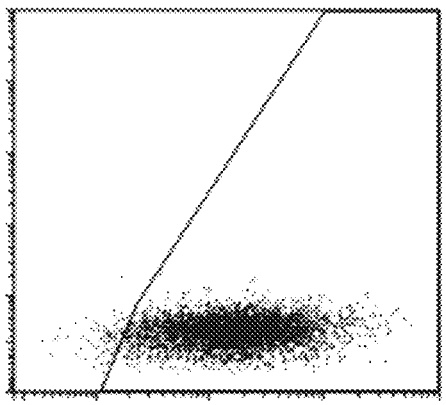
FIGS. 17A and 17B shows graphs of the measurement results obtained by a flow cytometer according to Reference Example 4.
Figure 17B:
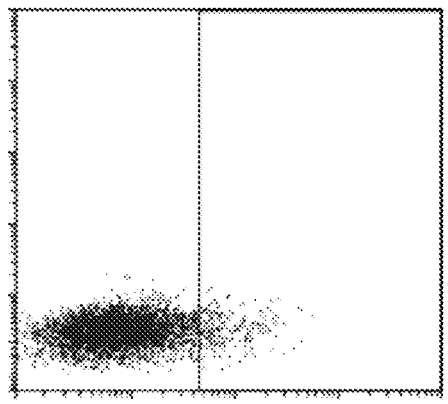
Figure 18:
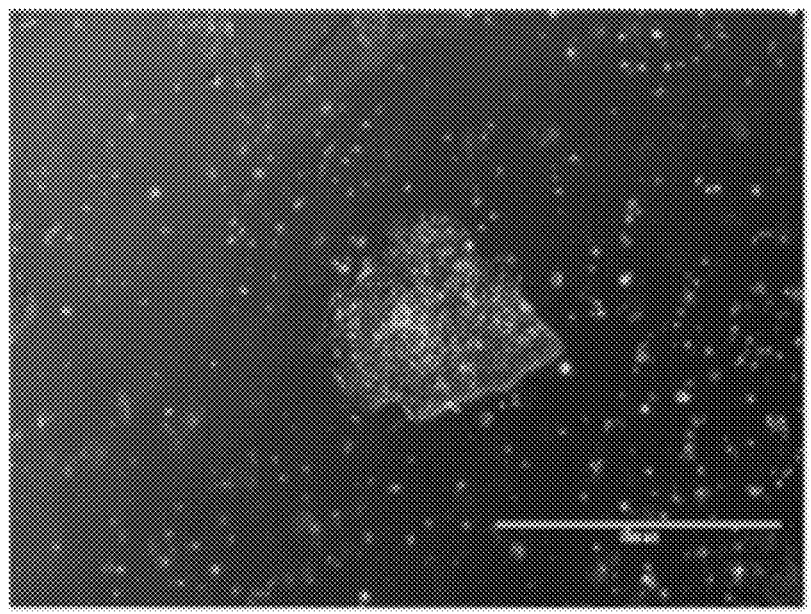
FIG. 18 is an image showing cells 15 days after infection according to Reference Example 4.
Figure 19A:
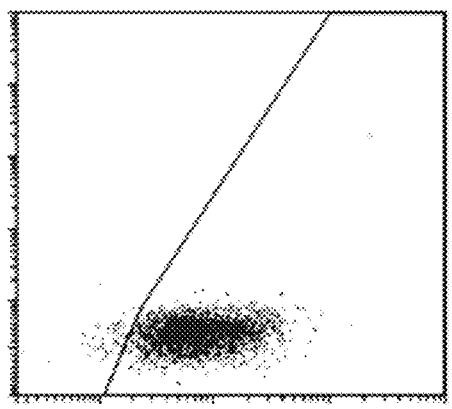
FIGS. 19A and 19B shows graphs of the measurement results obtained by a flow cytometer according to Reference Example 4.
Figure 19B:
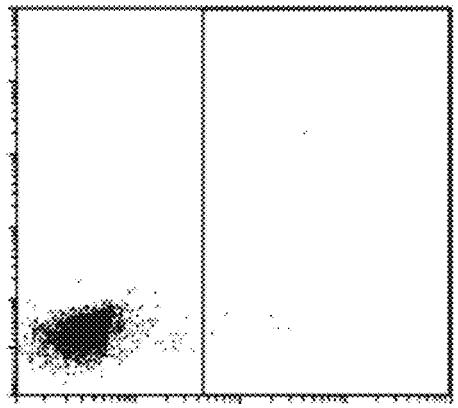
Figure 20:
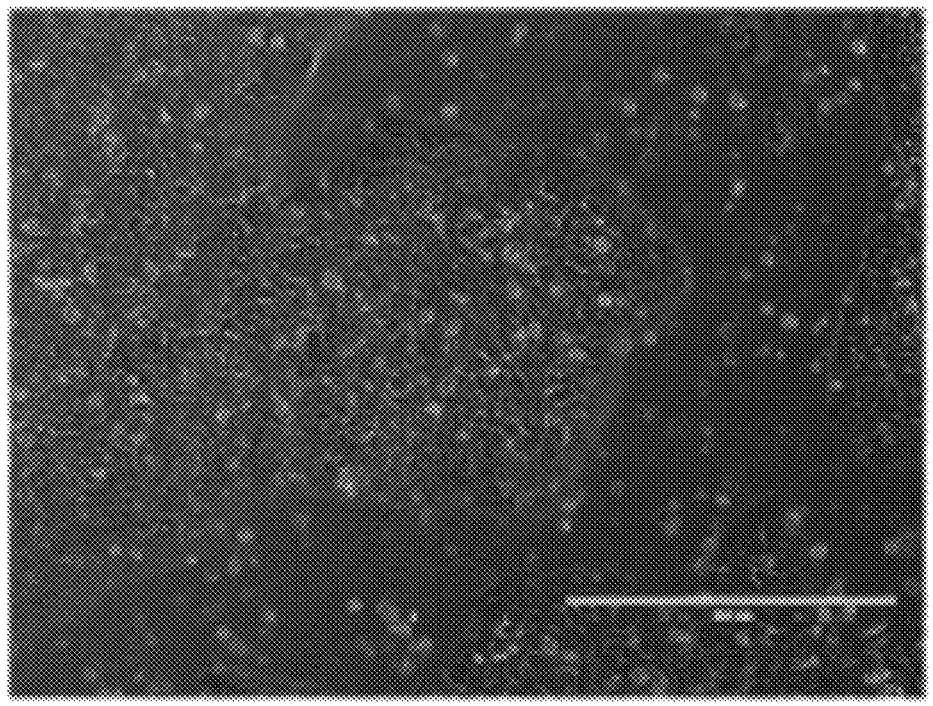
FIG. 20 is an image showing cells in the first passage according to Reference Example 4.

Using anti-Sendai virus antibodies, 15 days after infection, the cells before passage were stained, the Sendai virus remaining in the cells was evaluated with a flow cytometer, and the results are shown in FIGS. 17A and 17B. In addition, FIG. 18 shows an image of the cells 15 days after infection. The cells that were passaged once were stained using anti-Sendai virus antibodies, the Sendai virus remaining in the cells was evaluated with a flow cytometer, and the results are shown in FIGS. 19A and 19B. As shown in FIGS. 19A and 19B, in the first passage, the Sendai virus in the cells almost disappeared. FIG. 20 shows an image of the cells in the first passage.

Reference Example 5

SeV(PM)hKOS/TS12ΔF, SeV18+hKLF4/TSΔF, and SeV(HNL)hC-Myc/TS15ΔF were added to mononuclear cells that were three-dimensionally cultured in a polymer-containing blood medium so that the MOI was 5, a dish for inducing pluripotent stem cells was accommodated in an incubator at 37° C. and the cells were cultured. Two days after infection, the polymer-containing blood medium was replaced with a polymer-containing iPS cell medium. Then, the medium was replaced once every two days using the polymer-containing iPS cell medium.

14 days after infection, stem cell-like cell masses were generated. On the 14th day after infection, almost all cells were TRA1-60 positive cells. Here, when part of the obtained TRA1-60 positive cells were seeded and two-dimensionally cultured in a culture vessel, iPS cell-like colonies were formed. In addition, the cell masses were recovered using a mesh, a triple select as a cell-releasing agent was added to the recovered cells, the cells were left at room temperature for 5 minutes, the cell-containing solution was then sucked up, and the cell-containing solution was incubated at 37° C. for 5 minutes to 10 minutes. Then, an iPS cell medium was added, and the cell-containing iPS cell medium was recovered in a 15 mL tube. The number of cells was measured using a blood cell counting chamber, the concentration of the cell-containing solution was adjusted, the cells were seeded in the well plate so that the concentration was $0.25 \times 10^4$ cells/cm$^2$ or less, and the first passage was performed. In this case, 11 or more cells did not come into contact with each other. Next, the well-dish was accommodated in an incubator at 37° C., and cells were two-dimensionally cultured. Then, the cells were passaged so that the cells had 60% to 80% confluence. From the second passage onward, the cells were seeded in the well plate so that the concentration was $0.25 \times 10^4$ cells/cm$^2$ or less. In this case also, 11 or more cells did not come into contact with each other. Along the way, the temperature was raised to 38° C.

Figure 21:
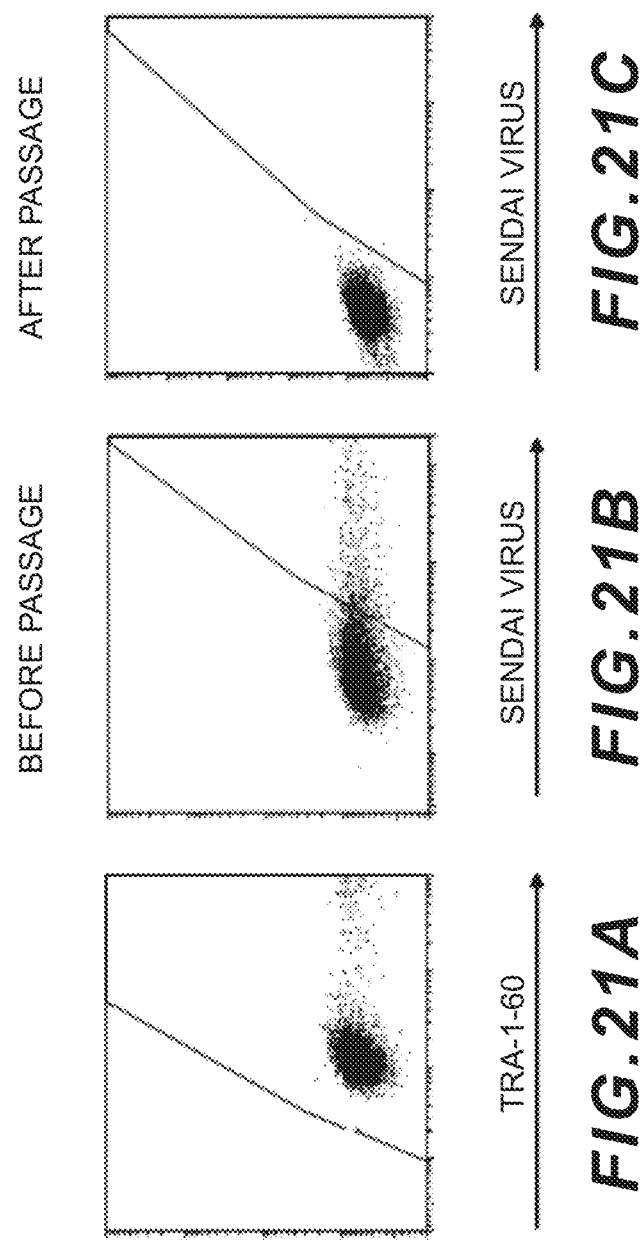
FIGS. 21A to 21C shows graphs of the measurement results obtained by a flow cytometer according to Reference Example 5.
Figure 22:
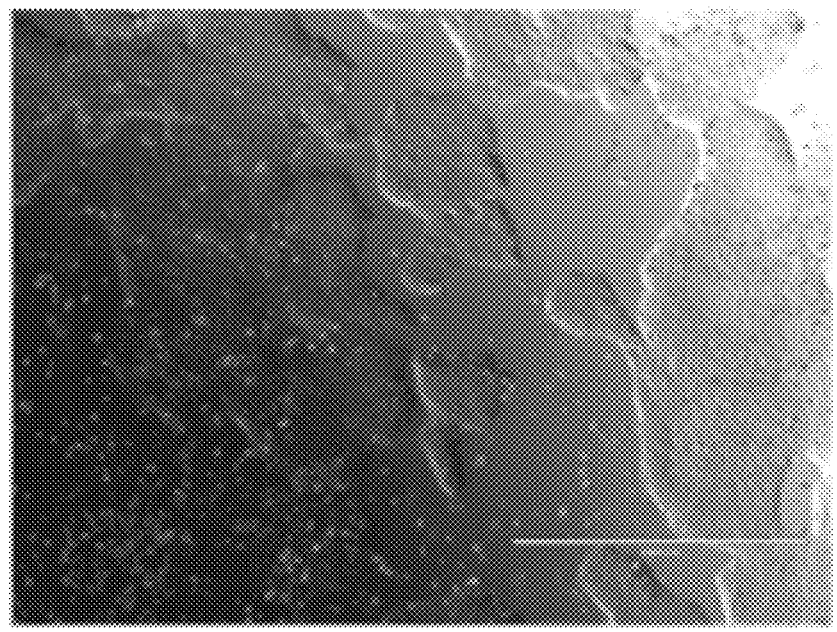
FIG. 22 is an image showing TRA1-60 positive cells according to Reference Example 5.

When the cells that were passaged twice were stained using anti-Sendai virus antibodies, and the Sendai virus remaining in the cells was evaluated with a flow cytometer, as shown in FIGS. 21A to 21C, the Sendai virus in the cells almost disappeared. FIG. 22 shows an image of the cells that were passaged twice.

Reference Example 6

SeV(PM)hKOS/TS12ΔF and SeV(HNL)hC-Myc/TS15ΔF were added to two-dimensionally cultured fibroblasts so that the MOI was 5, a dish for inducing pluripotent stem cells was accommodated in an incubator at 34° C., and the cells were cultured. Two days after infection, the blood medium was replaced with an iPS cell medium. Then, the medium was replaced once every two days using the iPS cell medium.

8 days after infection, stem cell-like cell masses were generated. On the 14th day after infection, almost all cells become TRA1-60 positive cells, and showed iPS cell-like morphology. 14 days after infection, a triple select as a cell-releasing agent was added to the dish and left at room temperature for 1 minute, and a cell-containing solution was then sucked up, and the cell-containing solution was incubated at 37° C. for 5 minutes to 10 minutes. Then, an iPS cell medium was added, and the cell-containing iPS cell medium was recovered in a 15 mL tube. The number of cells was measured using a blood cell counting chamber, the concentration of the cell-containing solution was adjusted, the cells were seeded in the well plate so that the concentration was $0.25 \times 10^4$ cells/cm$^2$ or less, and the first passage was performed. In this case, 11 or more cells did not come into contact with each other. Then, the well-dish was accommodated in an incubator at 37° C., and cells were two-dimensionally cultured. Then, the cells were passaged so that the cells had 60% to 80% confluence. From the second passage onward, the cells were seeded in the well plate so that the concentration was $0.25 \times 10^4$ cells/cm$^2$ or less. In this case also, 11 or more cells did not come into contact with each other.

Figure 23A:
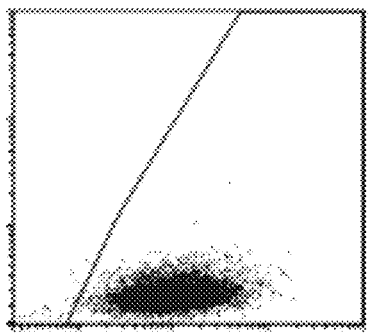
FIGS. 23A and 23B shows graphs of the measurement results obtained by a flow cytometer according to Reference Example 6.
Figure 23B:
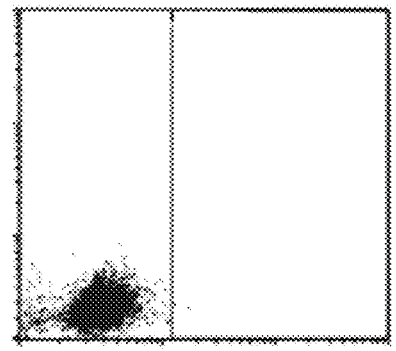
Figure 24:
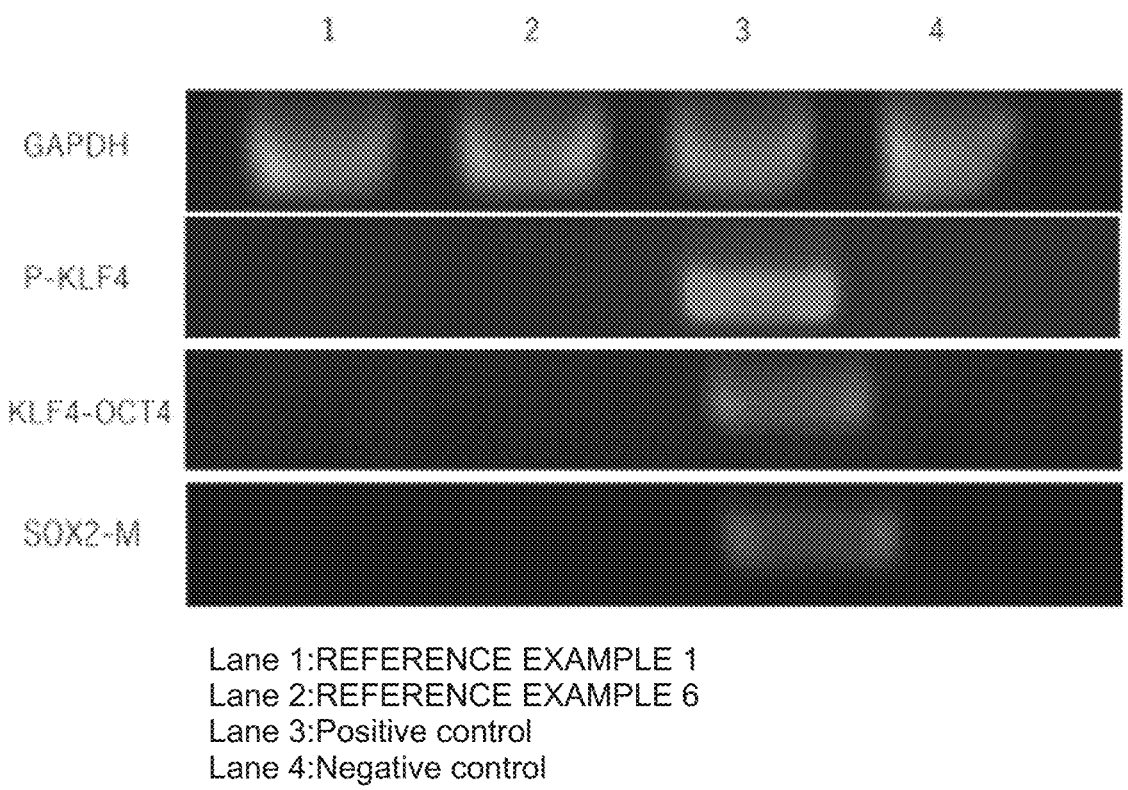
FIG. 24 is a graph showing PCR results according to Reference Example 6.
Figure 25:
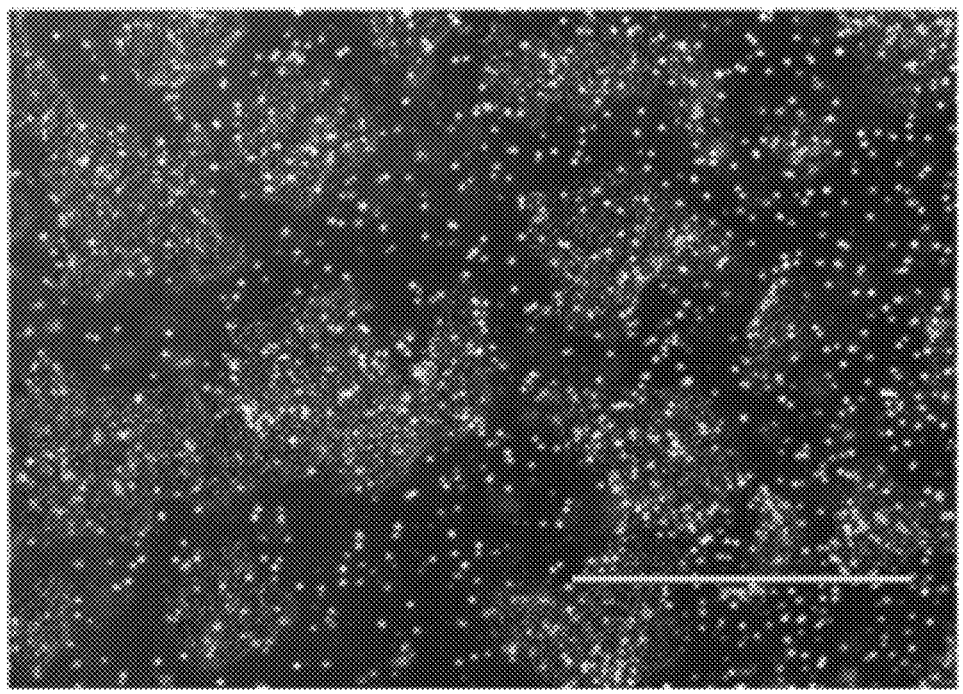
FIG. 25 is an image showing TRA1-60 positive cells according to Reference Example 6.

As shown in FIGS. 23A and 23B, when the cells were stained using anti-Sendai virus antibodies and the Sendai virus remaining in the cells was evaluated with a flow cytometer, the Sendai virus in the cells disappeared after the first passage. As shown in FIG. 24, the Sendai virus remaining in the cells was not detected by PCR. FIG. 25 shows an image of the obtained TRA1-60 positive cells.

Example 7 and Comparative Example 7

A DMEM containing 10% FBS was prepared as a medium for fibroblasts. Fibroblasts were suspended in a medium for adult human-derived fibroblasts to obtain a fibroblast suspension.

A solution in which 1.5 mL of PBS and 4.8 µL of silkworm-derived laminin (iMatrix-511 silk, nippi) were mixed was added to one well of a 6-well dish, and the dish was left in an incubator at 37° C. for 1 hour. Next, a solution in which PBS and laminin were mixed was removed from the well using an aspirator, and 1.5 mL of the fibroblast suspension was added to one well. The number of fibroblasts in one well was $0.5 \times 10^5$ to $2.0 \times 10^5$. Then, the fibroblasts were cultured in an incubator at 37° C. for 1 day.

Next, the medium was replaced with a stem cell induction medium. The amount of the medium replaced was 1.5 mL.

A tube A and a tube B were prepared, and 0.1 µL to 100 µL of a mixture containing OCT4 mRNA, SOX2 mRNA, KLF4 mRNA, and C-MYC mRNA (100 ng/µL) was added to 125 µL of PBS in the tube A. These RNAs were concentrated and purified through HPLC. 0.1 µL to 100 µL of a lipofection reagent was added to 125 µL of PBS in the tube B. Next, the solution in the tube A and the solution in the tube B were mixed, the mixed solution was left at room temperature for 10 minutes, and a total amount of the mixed solution was added to the medium in one well. Then, the dish was left in an incubator at 37° C. for 1 day, and the cells were transfected with RNA. Then, RNA transfection was repeated 11 times according to the same procedures.

The day after the 11$^{th}$ RNA transfection, the concentration of the cell-containing solution was adjusted, and the cells were seeded in a laminin-coated well plate for the first passage so that the concentration was $0.25 \times 10^4$ cells/cm$^2$ or less. In Example 7, all cells separated from the well plate were recovered during the first passage, and at least part of the recovered and mixed cells were seeded in the next well plate without distinguishing. On the other hand, in Comparative Example 7, colonies were picked and cloned during the first passage. Here, in both Example 7 and Comparative Example 7, cells were seeded so that 11 or more cells did not come into contact with each other during passage. Next, the well-dish was accommodated in an incubator at 37° C., and cells were two-dimensionally cultured. Then, the cells were passaged only once when the cells become 60% to 80% confluence. From the second passage onward, the cells were seeded in the well plate so that the concentration was $0.25 \times 10^4$ cells/cm$^2$ or less. In this case, 11 or more cells did not come into contact with each other.

Figure 26:
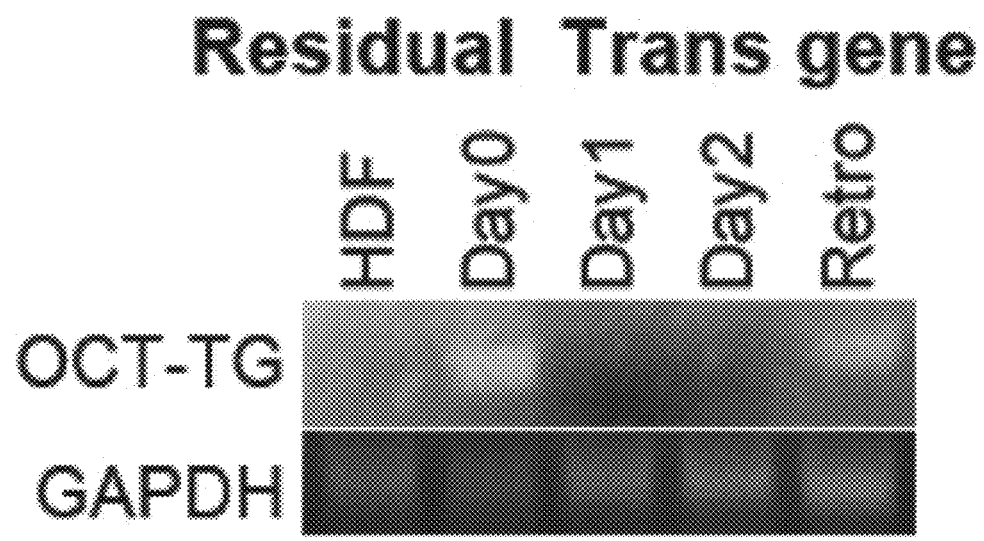
FIG. 26 is a graph showing the PCR results according to Example 7.
Figure 27:
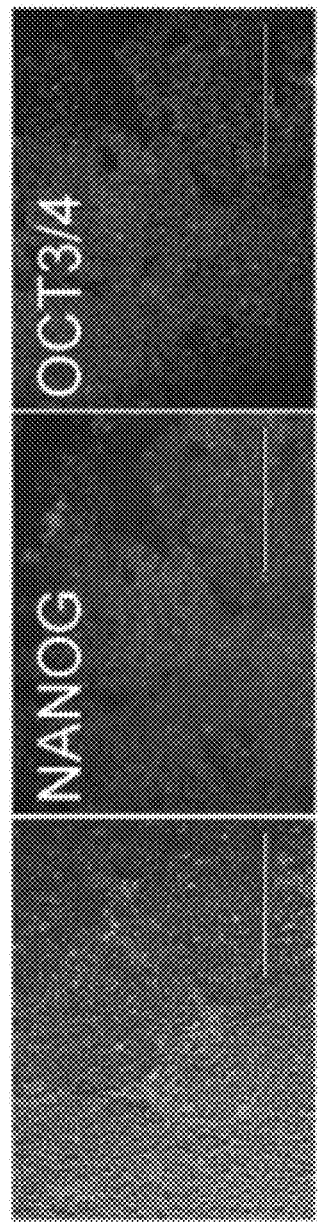
FIG. 27 shows images showing TRA1-60 positive cells according to Example 7.

As shown in FIG. 26, on the first day after the first passage, the reprogramming factor almost disappeared from the cells, and on the second day after the first passage, the reprogramming factor completely disappeared from the cells. On the 10$^{th}$ day from infection, almost all cells became TRA1-60 positive cells, and showed iPS cell-like morphology. FIG. 27 shows an immunostaining image of the TRA1-60 positive cells.

As in Example 1, the stem cells generated by the method according to Example 7 had a small variation in the clonal efficiency. As in Example 2, the stem cells generated by the method according to Example 7 had a stable proliferation rate and colony forming ability. As in Example 3, the stem cells generated by the method according to Example 7 had a small variation in the number of clamps and the number of cells after three-dimensional culture. As in Example 4, the stem cells generated by the method according to Example 7 had a stable ability to induce differentiation into cardiomyocytes. As in Example 5, the stem cells generated by the method according to Example 7 had a stable ability to induce differentiation into neural progenitor cells. As in Example 6, the stem cells generated by the method according to Example 7 had a stable ability to differentiate into the endoderm, the mesoderm, and the ectoderm.

As in Comparative Example 1, the stem cells generated by the method according to Comparative Example 7 had a large variation in the clonal efficiency. As in Comparative Example 2, the stem cells generated by the method according to Comparative Example 7 had a large variation in the proliferation rate and the colony forming ability. As in Comparative Example 3, the stem cells generated by the method according to Comparative Example 7 had a large variation in the number of clamps and the number of cells after three-dimensional culture. As in Comparative Example 4, the stem cells generated by the method according to Comparative Example 7 had an unstable ability to induce differentiation into cardiomyocytes. As in Comparative Example 5, the stem cells generated by the method according to Comparative Example 7 had an unstable ability to induce differentiation into neural progenitor cells. As in Comparative Example 6, the stem cells generated by the method according to Comparative Example 7 had an unstable ability to differentiate into the endoderm, the mesoderm, and the ectoderm.

Example 8

As in Example 1, the reprogramming factors were introduced into mononuclear cells. On the 14th day after infection, almost all cells become TRA1-60 positive cells, and showed iPS cell-like morphology. Then, in the stage in which cells were never passaged, the iPS cell-like cells were infected with the Sendai virus that can express Ngn2-Puro mRNA so that the MOI was 20. On the second day after infection with the Sendai virus, the medium in the well was replaced with a nerve induction medium (N3 medium) containing puromycin at a concentration of 2 μg/mL, and uninfected cells were killed. The N3 medium was prepared by adding 10 mL of B27, 5 mL of N2, and 1.6 mL of insulin at a concentration of 6.25 mg/mL to 500 mL of DMEMF12.

Figure 28:
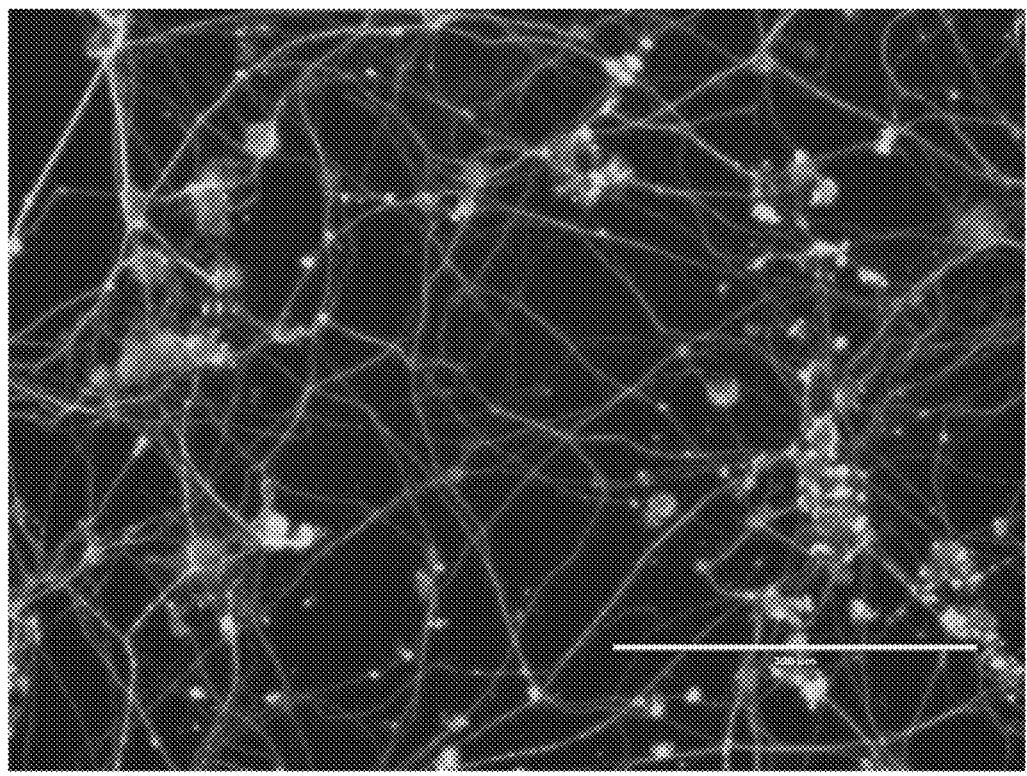
FIG. 28 is an image showing nervous system cells according to Example 8.
Figure 29A:
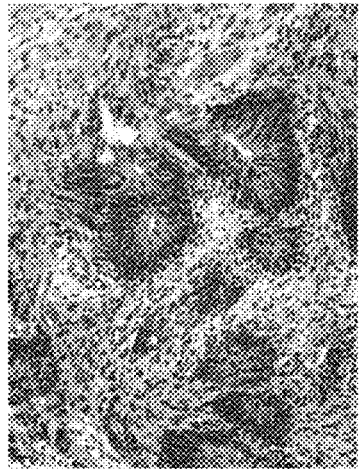
FIGS. 29A to 29D shows images of teratomas according to Example 9.
Figure 29B:
Figure 29C:
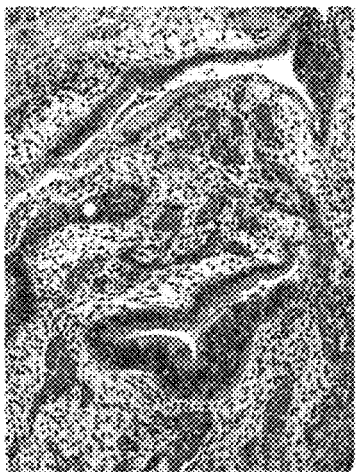
Figure 29D:
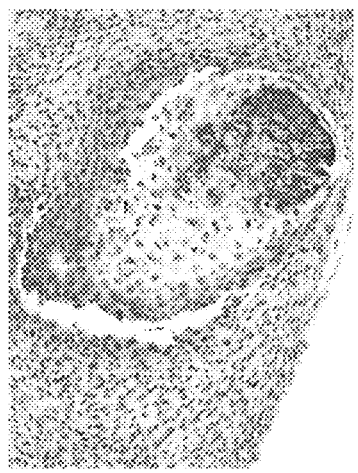

FIG. 28 shows a microscope image of the cells 14 days after infection with the Sendai virus. As shown in FIG. 28, it was morphologically confirmed that nervous system cells were induced from the cells after infection with the Sendai virus.

Example 9

As in Example 1, the reprogramming factors were introduced into mononuclear cells. On the 14th day after infection, almost all cells become TRA1-60 positive cells, and showed iPS cell-like morphology. Then, in the stage in which cells were never passaged, the iPS cell-like cells were transplanted into immunodeficient mouse testis. After a few weeks, teratomas were removed from the mouse, and a tissue section was prepared from the removed teratomas, and stained with hematoxylin and eosin (HE) and observed under a microscope. The results are shown in FIGS. 29A to 29D. A secretory tissue-like structure, a neural tube-like structure, an intestinal tract-like structure, a cartilage, and a bone-like structure were observed in the tissue section.

Figure 30:
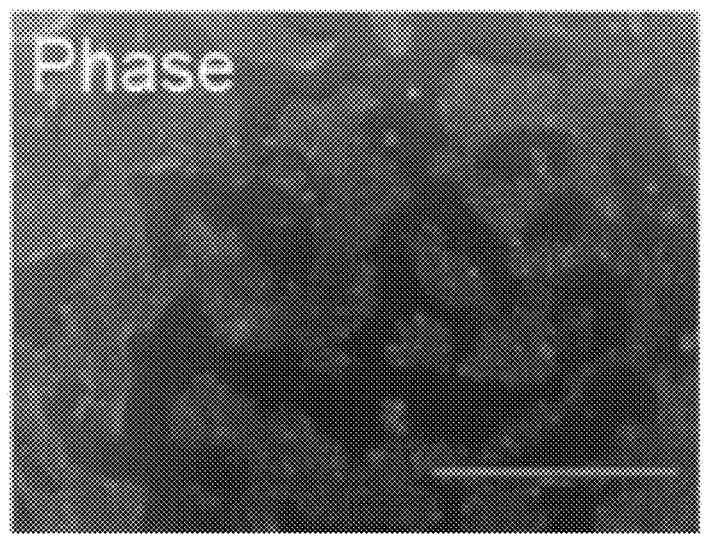
FIG. 30 is an image of iPS cell-like colonies according to Example 10.
Figures 31A, 31B:
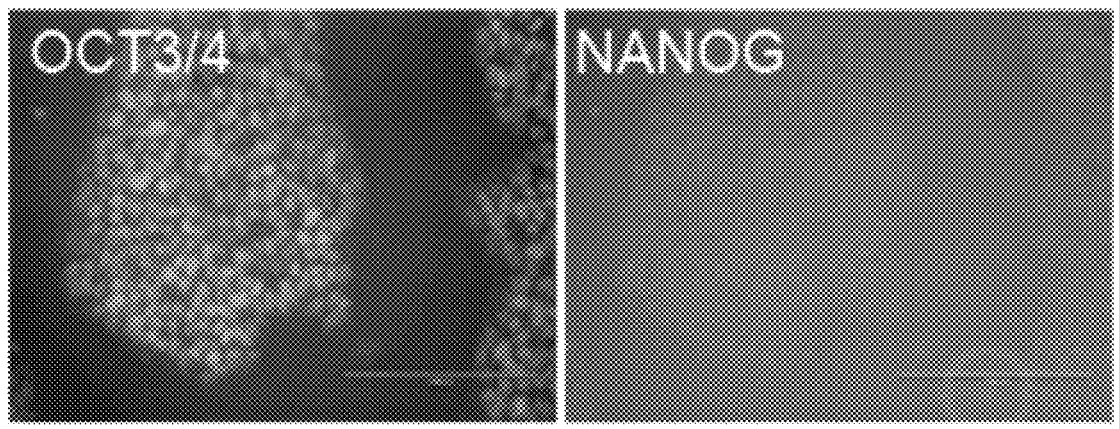
FIGS. 31A and 31B shows images of Oct3/4 positive cells and Nanog positive cells according to Example 10.
Figure 32:
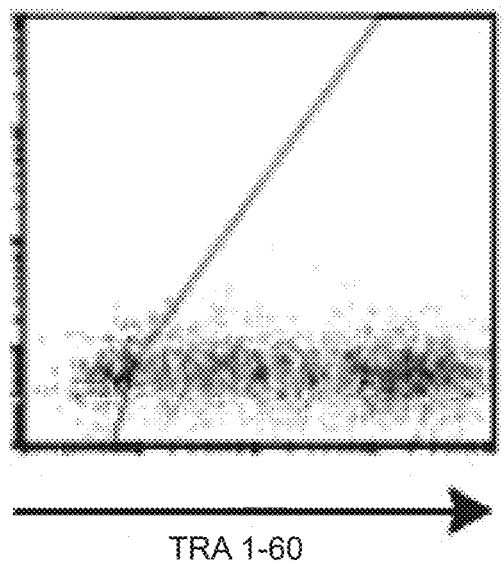
FIG. 32 is a dot plot obtained by a flow cytometer according to Example 10.

Example 10 mRNA was introduced into chimpanzee-derived fibroblasts in the same method as in Example 1 except that chimpanzee-derived fibroblasts were used. As a result, as shown in FIG. 30, formation of iPS cell-like colonies was observed. When the maintenance-cultured cells were immunostained with antibodies for Oct3/4, as shown in FIG. 31A, the cells showed Oct3/4 positive. In addition, when the maintenance-cultured cells were immunostained with antibodies for Nanog, as shown in FIG. 31B, the cells showed Nanog positive. In addition, as shown in FIG. 32, it was confirmed that the induced cells were TRA-1-60 positive.

Figure 33:
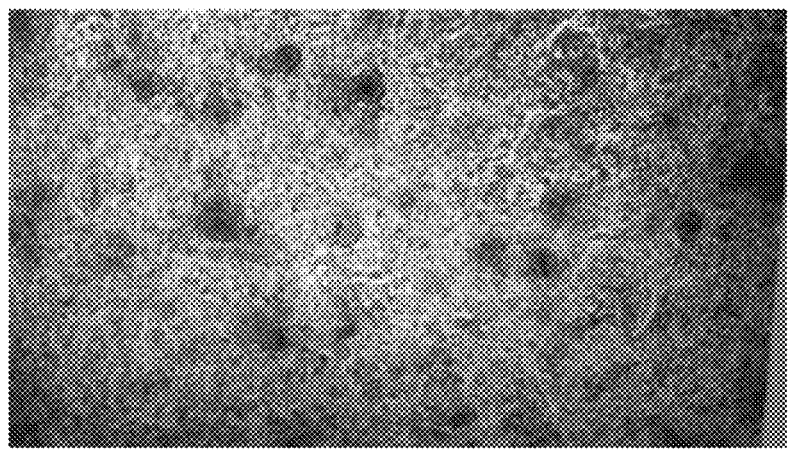
FIG. 33 is an image of cardiomyocytes according to Example 10.

The generated chimpanzee-derived stem cells were induced to differentiate into cardiomyocytes. FIG. 33 shows an image of the obtained cardiomyocytes.

Figure 34A:
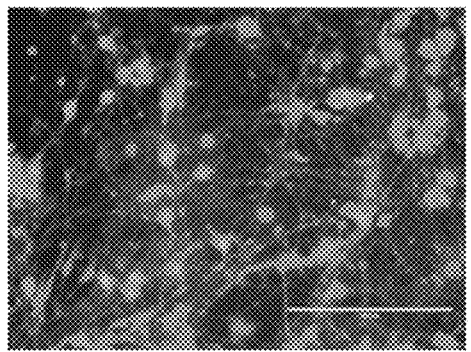
FIGS. 34A and 34B shows images of Munch13 positive cells and vGlut positive cells according to Example 10.
Figure 34B:
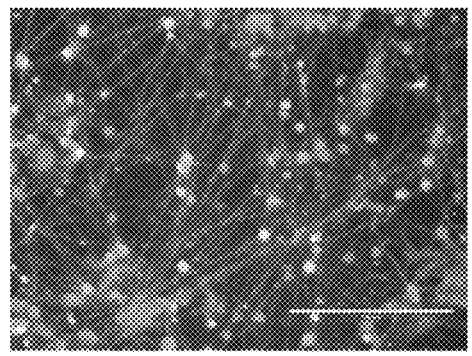

In addition, the generated chimpanzee-derived stem cells were induced to differentiate into nerve cells. FIGS. 34A and 34B shows images of the obtained cardiomyocytes. It was confirmed that the nerve cells were Munch13 positive and vGlut positive.

Example 11

Figure 35:
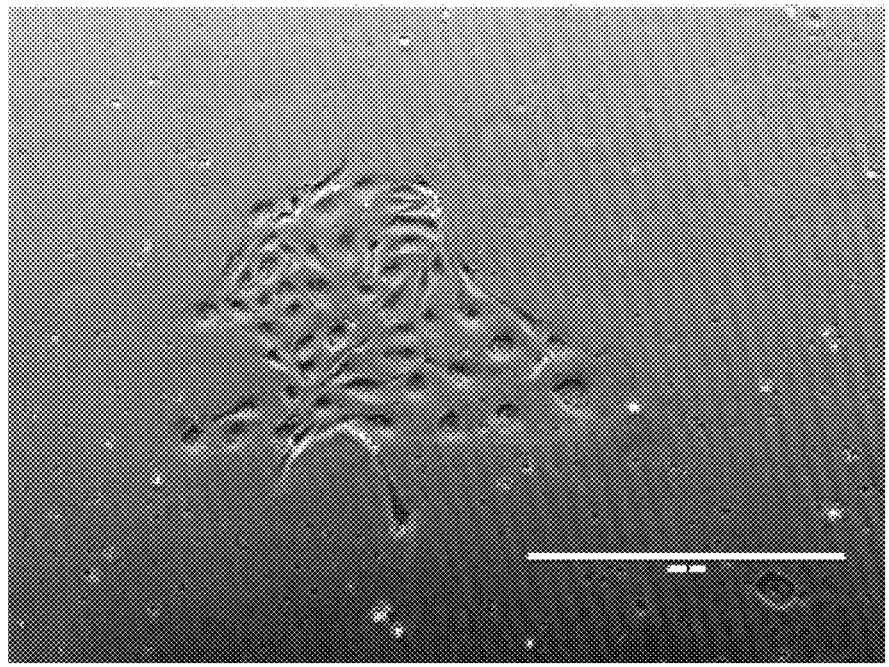
FIG. 35 is an image of urine-derived cells according to Example 11.
Figure 36:
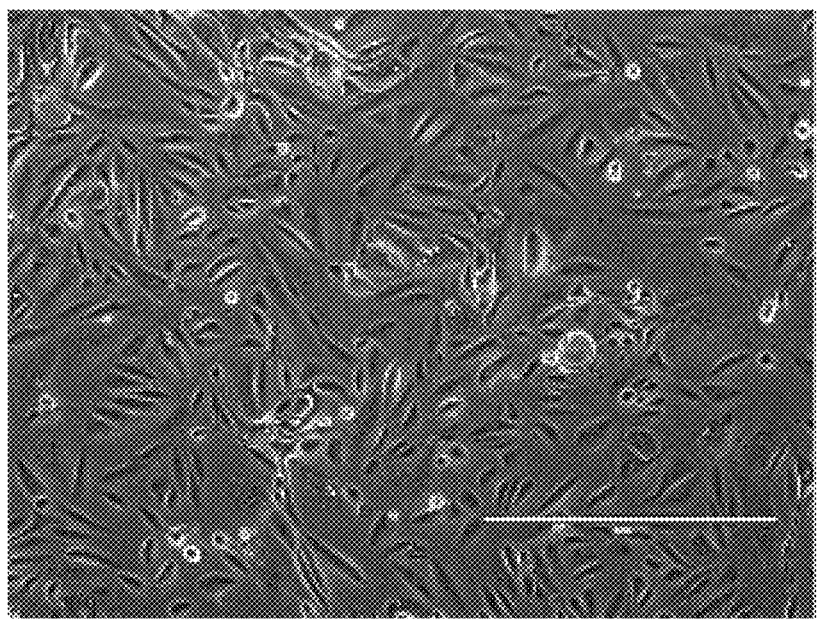
FIG. 36 is an image of urine-derived cells according to Example 11.

300 mL of urine was collected from a healthy subject, 6 urine samples were dispensed into a 50 mL Falcon tube, and the tube was centrifuged at 400G for 5 minutes. After centrifugation, the supernatant was removed from the tube, 30 mL of PBS was put into the tube, and the tube was centrifuged at 400G for 5 minutes. After centrifugation, the supernatant was removed from the tube, 30 mL of a primary medium was put into the tube, and the tube was centrifuged at 400G for 5 minutes. A primary medium was prepared by adding fetal bovine serum (Gibco, 10437028, final concentration 100), SingleQuots Kit CC-4127 REGM (Lonza, 1/1,000 amount), and Antibiotic-Antimycotic (Gibco, 15240062, 1/100 amount) to DMEM/Ham's F12 (Gibco, 11320-033). After centrifugation, the supernatant was removed from the tube, cells were suspended in 1 mL of the primary medium, the cells were seeded in one well of a gelatin-coated 24-well plate, and the cells were incubated in an incubator at 37° C. For 2 days after the cells were seeded, the primary medium was added to a 300 μL well, and from the $3^{rd}$ day onward, the medium was replaced using a medium for epithelial cells. The medium for epithelial cells was prepared by adding SingleQuots Kit CC-4127 REGM (Lonza) to a renal epithelial cell basal medium (Lonza). FIG. 35 shows a microscope image of the cells after expanded and cultured for 6 days. The cells were subjected to the first passage on the $7^{th}$ days after seeding, the cells were additionally expanded and cultured, and the cells were subjected to the second passage on the $7^{th}$ day after the first passage. FIG. 36 shows a microscope image of the cells on the 6th day after the second passage.

Example 12

Figure 37B:
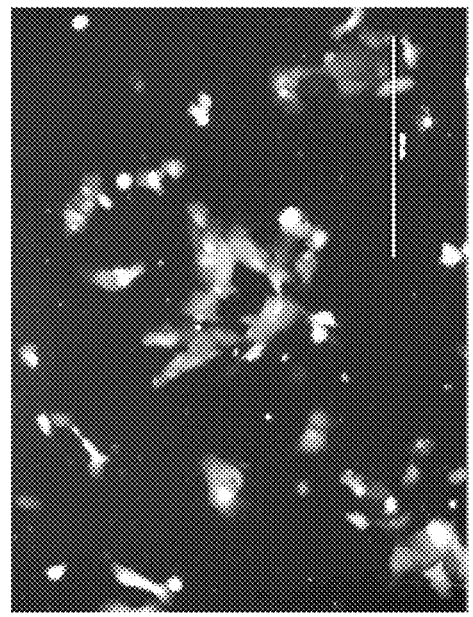
FIGS. 37A and 37B shows images of urine-derived cells transfected with RNA encoding GFP according to Example 12.
Figure 37A:
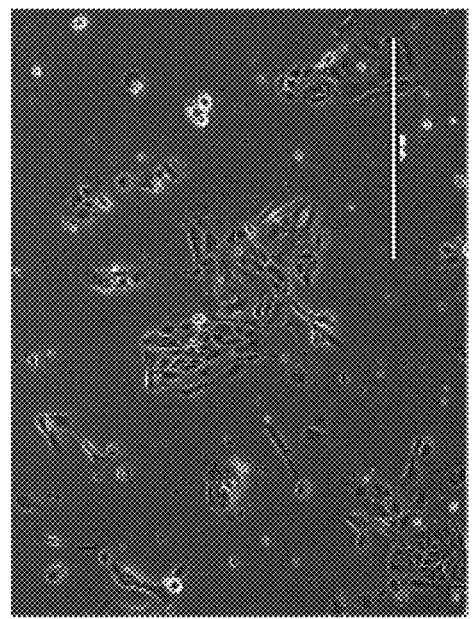
Figure 38A:
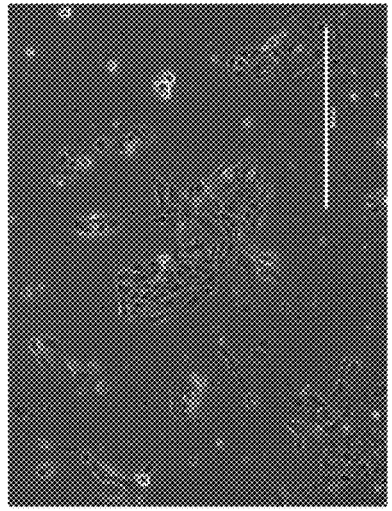
Figure 38C:
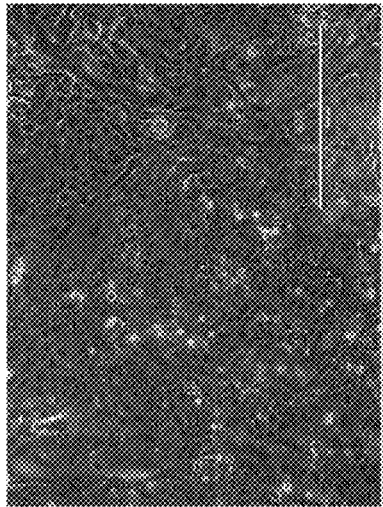
Figure 38D:
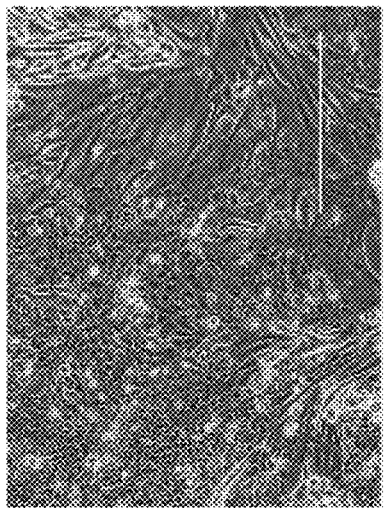

A dish coated with laminin 511 was used as a dish for inducing pluripotent stem cells. $1 \times 10^4$ to $1 \times 10^5$ urine-derived cells prepared in Example 11 were seeded in the dish for inducing pluripotent stem cells and incubated at 37° C. For the medium, a medium for epithelial cells was used. The next day, a mixture containing a transfection reagent and RNA that encodes a green fluorescent protein (GFP) was added to a medium, the medium was replaced with the above medium, and incubated at 37° C. FIGS. 37A and 37B shows microscope images of the cells on the next day. Expression of GFP was observed, which indicates that transfection into urine-derived cells was performed.

Example 13

A dish coated with laminin 511 was used as a dish for inducing pluripotent stem cells. $1 \times 10^4$ to $1 \times 10^5$ urine-derived cells prepared in Example 11 were seeded in the dish for inducing pluripotent stem cells and incubated at 37° C. For the medium, a medium for epithelial cells was used. The next day, a tube A and a tube B were prepared, 0.1 μL to $10^2$ μL of a mixture containing $M_3O$ mRNA, SOX2 mRNA, KLF4 mRNA, C-MYC mRNA, and LIN28 mRNA (100 ng/μL) was added to 125 μL of PBS in the tube A. These RNAs were modified with pseudouridine (Ψ). In addition, these RNAs were substantially concentrated and purified into single-stranded RNA through HPLC. It was confirmed that the ratio ($A_{260}/A_{280}$) of the absorbances of RNA at 260 nm and 280 nm was 1.71 to 2.1, and proteins were not substantially mixed. In addition, when dot-blotting analysis was performed using anti-double-stranded RNA antibody J2, 90% or more of double-stranded RNA was removed. 0.1 μL to 100 μL of a lipofection reagent was added to 125 μL of PBS in the tube B. Next, the solution in the tube A and the solution in the tube B were mixed, the mixed solution was left at room temperature for 10 minutes, a total amount of the mixed solution was added to a transfection medium without using B18R or the like, the medium was replaced using the transfection medium, and incubated at 37° C. Transfection was performed once daily for 10 days. Observation was performed on days 1, 5, 7, and 14 after cell seeding. As shown in FIGS. 38A to 38D, it was observed that cell morphology changed like ES cells as the day progressed.

Example 14

Figure 39:
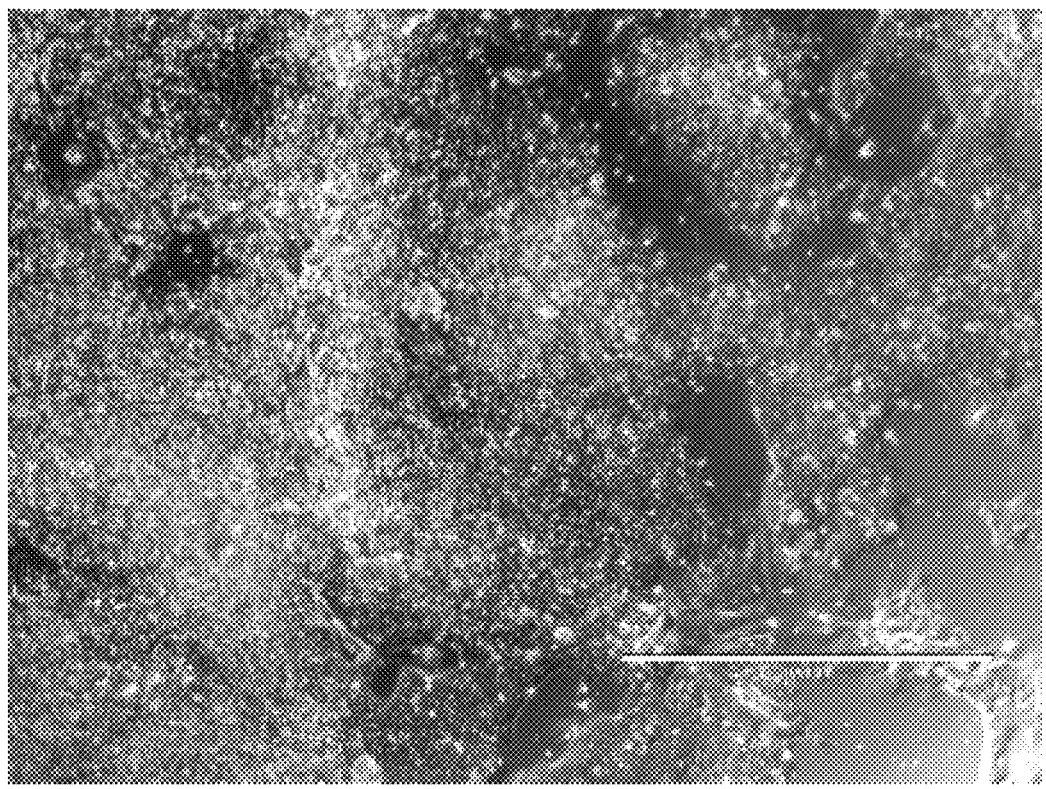
FIG. 39 is an image of urine-derived cells into which reprogramming factors were introduced according to Example 14.

As in Example 13, urine-derived cells were transfected for 10 days. The cells were cultured in a medium for stem cells (StemFit, Ajinomoto) from the 11$^{th}$ day after the cells were seeded, all cells were separated from the dish on the 14th day, and part of the recovered and mixed cells were seeded and passaged in the medium. During passage, without picking up colonies, all cells on the dish were recovered, and $1\times10^2$ to $1\times10^5$ cells were seeded on the dish. FIG. 39 shows a microscope image of the cells 6 days after passage. ES cell-like cells were confirmed.

Example 15

Figure 40A:
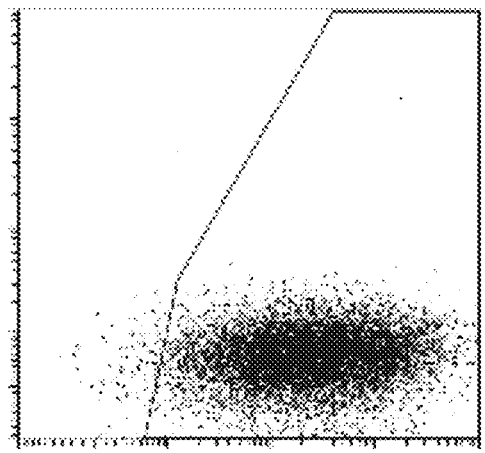
FIGS. 40A and 40B shows dot plots obtained by a flow cytometer according to Example 15.
Figure 40B:
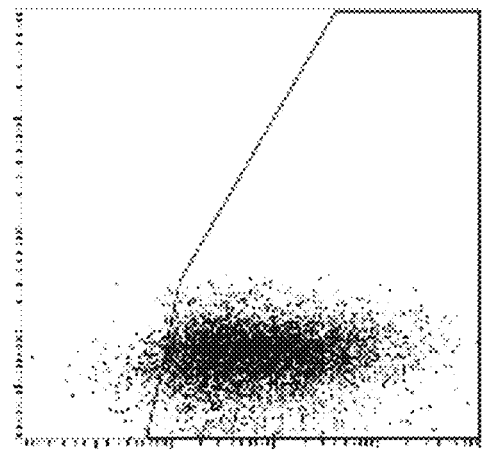

As in Example 13, urine-derived cells were transfected for 10 days. When the cells were cultured in a medium for stem cells (StemFit, Ajinomoto) from the 11$^{th}$ day after the cells were seeded, the cells were separated from the dish on the 14$^{th}$ day, and part of the cells were analyzed using a flow cytometry, as shown in FIG. 40A, TRA-1-60 positive was confirmed. In addition, when the cells separated from the dish on the 14$^{th}$ day were passaged, and analyzed using a flow cytometry 7 days later, as shown in FIG. 40B, TRA-1-60 positive was confirmed.

Example 16

Figure 41A:
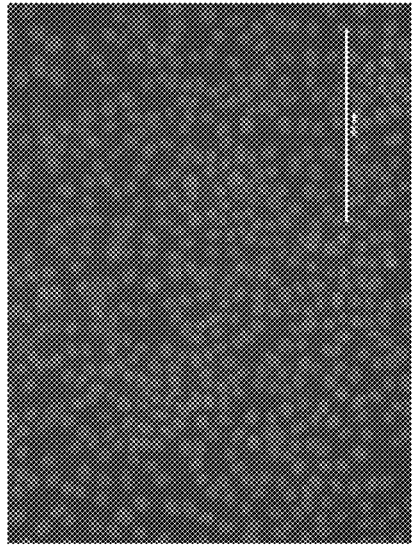
FIGS. 41A to 41D shows images of urine-derived cells into which reprogramming factors were introduced according to Example 16.
Figure 41B:
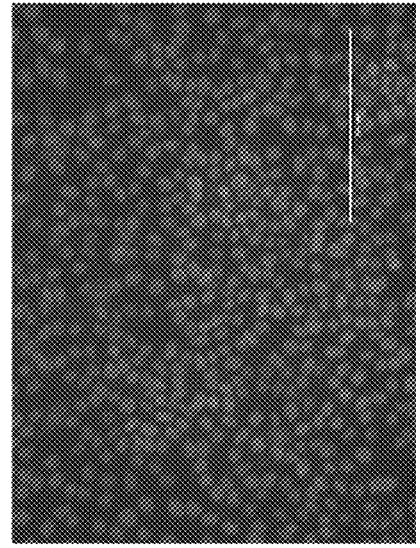
Figure 41C:
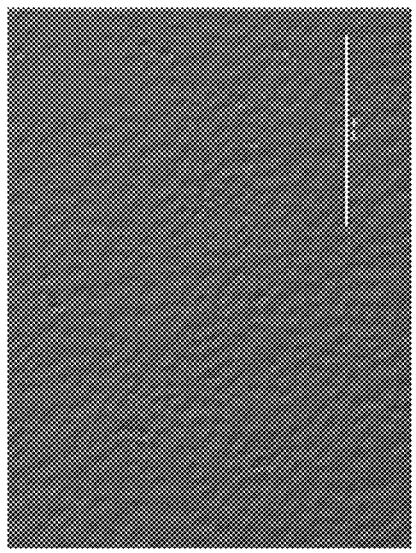
Figure 41D:
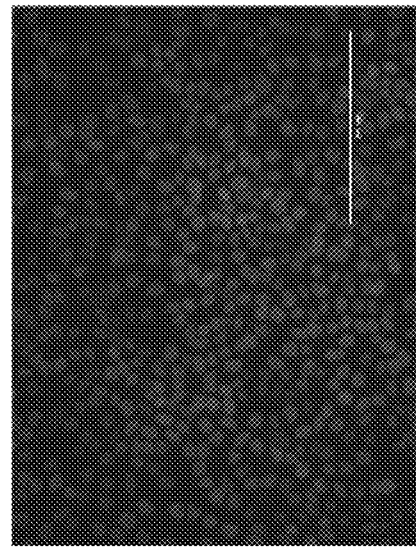

As in Example 13, urine-derived cells were transfected for 10 days. The cells were cultured in a medium for stem cells (StemFit, Ajinomoto) from the 11$^{th}$ day after the cells were seeded, all cells were separated from the dish on the 14th day, and part of the separated and mixed cells were seeded and passaged. StemFit (registered trademark) was used as the medium after passage. 7 days after passage, cells were immobilized, and the cells were stained using anti-OCT3/4 antibodies and anti-NANOG antibodies. In addition, nuclei chemical staining using Hoechst (registered trademark) was performed. As a result, as shown in FIGS. 41A to 41D, expression of OCT3/4 and NANOG, which are specific markers for pluripotent stem cells, in cell nuclei was confirmed. Therefore, it was shown that the pluripotent stem cells could be induced from urine-derived cells using RNA. Here, FIG. 41D is an image obtained by synthesizing an image of cells stained using anti-OCT3/4 antibodies, an image of cells stained using anti-NANOG antibodies, and an image of cells stained using Hoechst (registered trademark).

Example 17

Figure 42B:
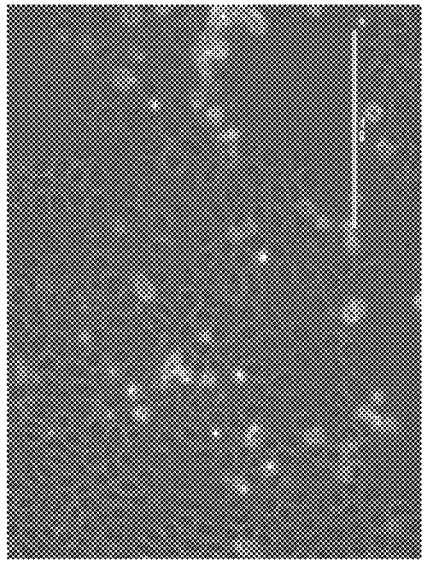
FIGS. 42A to 42D shows images of urine-derived cells into which reprogramming factors were introduced according to Example 16.
Figure 42D:
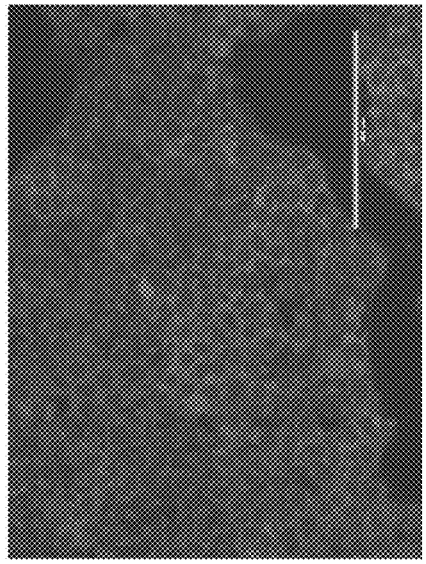
Figure 42A:
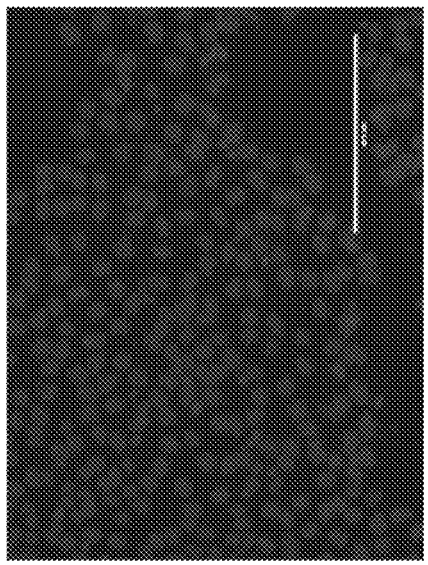
Figure 42C:
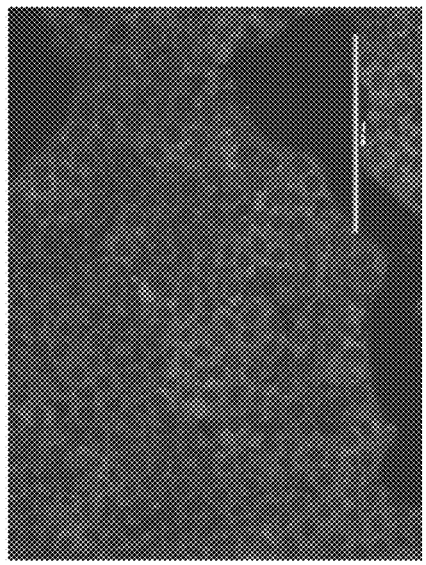

As in Example 13, urine-derived cells were transfected for 10 days. The cells were cultured in a medium for stem cells (StemFit, Ajinomoto) from the 11$^{th}$ day after the cells were seeded, all cells were separated from the dish using a triple select on the 14$^{th}$ day, and part of the separated and mixed cells were seeded and passaged in a medium. StemFit (registered trademark) was used as the medium after passage. 7 days after passage, cells were immobilized, and the cells were stained using anti-LIN28 antibodies. In addition, nuclei chemical staining using Hoechst (registered trademark) was performed. As a result, as shown in FIGS. 42A to 42D, expression of LIN28, which is a specific marker for pluripotent stem cells, in cell nuclei was confirmed. Therefore, it was shown that the pluripotent stem cells could be induced from urine-derived cells using RNA. Here, FIG. 42D is an image obtained by synthesizing an image of cells stained using anti-LIN28 antibodies and an image of cells stained using Hoechst (registered trademark).

What is claimed is:

1. A method for producing induced pluripotent stem cells (iPSCs), comprising:
   (a) collecting cells from urine;
   (b) introducing reprogramming factors into the collected cells, wherein the reprogramming factors comprise an OCT mRNA, a SOX mRNA, a KLF mRNA, and a MYC mRNA;
   (c) culturing the cells introduced with the reprogramming factors until pluripotent stem cells are induced from the introduced cells;
   (d) recovering all the cultured cells; and
   (e) seeding at least a part of the recovered cells in a medium to passage the seeded cells,
   wherein the method does not include isolating a plurality of colonies formed by the cultured cells or cloning a single colony formed by the cultured cells.

2. The method according to claim 1, wherein the seeded cells are not cloned after the passage.

3. The method according to claim 1,
   wherein in the culturing, the cells introduced with the reprogramming factors are adherently cultured in a culture vessel, and
   in the recovering, all the cells attached to the culture vessel are recovered.

4. The method according to claim 1, wherein the seeded cells are passaged without distinguishing them according to a gene expression state.

5. The method according to claim 1, wherein the seeded cells are passaged without distinguishing the degree of reprogramming of the seeded cells.

6. The method according to claim 1, further comprising freezing the cells introduced with the reprogramming factors.

7. The method according to claim 1, further comprising differentiating the iPSCs into at least one selected from among the endoderm, the mesoderm, and the ectoderm.

8. The method according to claim 1, further comprising forming at least one selected from among embryoid bodies, organoids, and spheres from the iPSCs.

9. The method according to claim 1, further comprising inducing somatic cells from the iPSCs, wherein the somatic cells are not pluripotent stem cells.

10. The method according to claim 9, further comprising cloning the induced somatic cells.

11. The method according to claim 1, further comprising performing a gene editing treatment on the iPSCs.

12. The method according to claim 1, wherein the collected cells are bladder epithelial cells.

13. The method according to claim 1, wherein the urine is collected from a plurality of humans or a plurality of non-human animals.

14. The method according to claim 1, wherein the cells introduced with the reprogramming factors are cultured in a closed culture vessel.

15. A method for producing induced pluripotent stem cells, comprising:
   (a) collecting cells from urine;
   (b) introducing reprogramming factors into the collected cells, wherein the reprogramming factors comprise an OCT mRNA, a SOX mRNA, a KLF mRNA, and a MYC mRNA;
   (c) culturing the cells introduced with the reprogramming factors until pluripotent stem cells are induced from the introduced cells;

(d) recovering all the cultured cells; and
(e) inducing somatic cells from the induced pluripotent stem cells without passaging,
wherein the method does not include isolating a plurality of colonies formed by the cultured cells or cloning a single colony formed by the cultured cells.

16. The method according to claim 15, further comprising freezing the cells introduced with the reprogramming factors.

17. The method according to claim 15, further comprising inducing at least one selected from among the endoderm, the mesoderm, and the ectoderm from the induced pluripotent stem cells.

18. The method according to claim 15, wherein the cells introduced with the reprogramming factors are cultured in a closed incubator.

* * * * *